US010712324B2

(12) United States Patent
Hansmann et al.

(10) Patent No.: US 10,712,324 B2
(45) Date of Patent: Jul. 14, 2020

(54) DEVICE WITH A PUMPING DEVICE FOR TESTING THE OPERATIONAL CAPABILITY OF A GAS GUIDE ELEMENT OF A GAS-MEASURING SYSTEM

(71) Applicant: Drägerwerk AG & Co. KGaA, Lübeck (DE)

(72) Inventors: Hans-Ullrich Hansmann, Barnitz (DE); Henning Gerder, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 354 days.

(21) Appl. No.: 15/817,849

(22) Filed: Nov. 20, 2017

(65) Prior Publication Data
US 2018/0143171 A1 May 24, 2018

(30) Foreign Application Priority Data
Nov. 23, 2016 (DE) .................. 10 2016 013 958

(51) Int. Cl.
*G01N 33/00* (2006.01)
*G01M 3/22* (2006.01)
*G01M 3/28* (2006.01)

(52) U.S. Cl.
CPC .......... *G01N 33/007* (2013.01); *G01M 3/222* (2013.01); *G01M 3/2807* (2013.01); *G01M 3/2846* (2013.01); *G01N 2033/0072* (2013.01)

(58) Field of Classification Search
CPC ........... G01N 33/07; G01N 2033/0072; G01N 33/0006; G01N 33/0008; G01N 33/007; E21B 47/1025; G08B 21/20; G01M 3/18; G01M 3/182; G01M 3/183; G01M 3/04; G01M 3/08; G01M 3/083; G01M 3/085
(Continued)

(56) References Cited

U.S. PATENT DOCUMENTS 2,353,287 A * 7/1944 Benesh ............... G01M 3/2807
405/54
6,237,392 B1 5/2001 Yu et al.
(Continued)

FOREIGN PATENT DOCUMENTS

DE 10 2005 045 272 B4 10/2007
DE 20 2006 020 536 U1 11/2008
(Continued)

*Primary Examiner* — Robert R Raevis
(74) *Attorney, Agent, or Firm* — McGlew and Tuttle, P.C.

(57) ABSTRACT

A device (1) includes a pumping device (7) and a control unit (70) and is configured to test the operational capability of a gas guide element (3) in a gas-measuring system (11) that includes a gas sensor (5). The control unit (70) carries out steps with two operating states including delivering a test gas (91) by the pumping device (7) through the gas guide element (3) to a remote measuring location (80) and is subsequently delivered from the measuring location (80) to the gas sensor (5). Measured values of a gas concentration are detected by the gas sensor (5) during the delivery from the remotely located measuring location (80) to the gas sensor (5) and analyzed to determine whether changes occurring in the detected gas concentration during the delivery from the measuring location (80) to the gas sensor (5) indicate whether the gas guide element (3) is capable of operating.

14 Claims, 9 Drawing Sheets

(58) Field of Classification Search
USPC .......... 73/1.06, 1.01, 37, 40, 40.5 R, 40.5 A, 73/49.1
See application file for complete search history.

(56) References Cited

U.S. PATENT DOCUMENTS

| | | |
|---|---|---|
| 7,406,854 B2 | 8/2008 | Lange et al. |
| 7,645,367 B2 | 1/2010 | Tschuncky et al. |
| 9,063,105 B2 | 6/2015 | Berndt et al. |
| 2018/0143170 A1* | 5/2018 | Hansmann ......... G01N 33/0008 |

FOREIGN PATENT DOCUMENTS

| | | |
|---|---|---|
| DE | 10 2013 008 425 B3 | 5/2014 |
| DE | 10 2014 221 499 A1 | 4/2016 |
| DE | 10 2015 003 745 A1 | 9/2016 |
| DE | 10 2015 015 152 A1 | 6/2017 |
| SG | 10201508959 A1 | 6/2016 |
| TW | 431600 U | 4/2001 |
| WO | 99/17110 A1 | 4/1999 |
| WO | 0073868 A1 | 12/2000 |
| WO | 2007/087 403 A2 | 8/2007 |

\* cited by examiner

DEVICE WITH A PUMPING DEVICE FOR TESTING THE OPERATIONAL CAPABILITY OF A GAS GUIDE ELEMENT OF A GAS-MEASURING SYSTEM

CROSS REFERENCE TO RELATED APPLICATIONS

This application claims the benefit of priority under 35 U.S.C. § 119 of German Application 10 2016 013 958.7, filed Nov. 23, 2016, the entire contents of which are incorporated herein by reference.

FIELD OF THE INVENTION

The present invention pertains to a device with a pumping device for testing the operational capability of a gas guide element in a gas-measuring system.

BACKGROUND OF THE INVENTION

Gas-measuring systems are used for industrial gas measurement and protect persons who are located in areas or rooms from hazards to health and life. Industrial gas measurement is important in an industrial environment, such as in the petrochemical industry, refineries, chemical industry, for monitoring explosive or toxic gases or vapors. Both mobile and stationary devices are used for these applications. Combinations of mobile or stationary devices are also used to make it possible to perform gas concentration measurements or gas analysis in storage tanks, boreholes or silos.

Thus, a combination of a mobile gas-measuring device and a pump is known from DE 10 2005 045 272 B4. It is thus possible to also use mobile gas-measuring devices for measuring gas concentrations in a main shaft, tank or in a borehole. Gas can be delivered to the gas-measuring device by means of the pump and an element for gas delivery, preferably a hose line. The pump is controlled in terms of the start of delivery, flow rate, end of delivery and other operating characteristics of the pump by the mobile gas-measuring device or the control thereof.

A possibility for testing a sensor system and a hose line of a gas-measuring system, which can be carried out essentially only once, is known from DE 10 2015 003 745 from the area of mobile gas measuring technology. A quantity of gas sample positioned at the end of the hose is introduced into the hose line by means of a remote release and fed to the gas-measuring system, so that testing of the sensor system and of the hose line is made possible.

A gas sensor with an adapter is known from U.S. Pat. No. 7,406,854 B2. The adapter is configured to form a port of a hose line. It is possible via this hose line to feed gas from a remotely located measuring location to the gas sensor. This delivery of gas may be carried out, for example, by means of a feed pump.

Gas-measuring systems comprising a gas sensor and a gas generator are known from WO 1999/17110 A1 as well as U.S. Pat. No. 7,645,367. Such combinations of gas generators and gas sensors make it possible to test the measuring properties of the gas sensors, especially to determine whether the gas sensor responds sensitively to the admission of a measured gas concentration generated by the gas generator.

A device for testing a gas sensor is known, for example, from DE 20 2006 020 536 U1. A gas generator, which is suitable for generating ethane, is described. The gas generator is intended for testing the gas sensor and is configured to dispense a certain quantity of a gas to/into the gas sensor, and a change or response of the output signal of the gas sensor, which change or response is based on this, is an indication that the gas sensor is able to function.

Recommendations have been issued by the Occupational Safety and Health Administration (OSHA) of the U.S.A. concerning function tests with so-called "bump tests," wherein a regular testing of gas sensors can be carried out by means of suitable adapters and a suitable gas.

U.S. Pat. No. 7,406,854 B2 describes an adapter for testing or calibrating an electrochemical gas sensor. The adapter can preferably be arranged on the gas sensor with a Velcro fastener and can be removed again from same after the testing or calibration has been carried out.

The state of the art cited does not show any solutions for the repeated or regular testing of the operational capability in gas-measuring systems with gas feed lines or hose lines that are provided for feeding gas from a remotely located measuring location to a gas sensor system and are arranged in the gas-measuring systems. Ensuring the functional capability of the feed lines or hose lines as well as the connection elements thereof is just as essential for a reliable operation of the gas-measuring systems as the operational capability of the gas sensor system itself. Leaks in the gas feed lines, hose lines or connection elements (plugs, couplings, sockets, bonded joints, soldered connections, welded connections) bring about changes in the gas concentrations on the way from the measuring location to the gas sensor system, which may cause as a consequence an incorrect measurement with consequential incorrect assessments, measured value outputs and alarms concerning current situations at the measuring location. Leaks result, for example, from holes, cracks, kinks or porous partial sections in hose lines as well as from holes, for example, those caused by material fatigue in systems and corresponding screwed, plug-type or soldered connections or line couplings.

A regular, repeatable testing of the operational capability of the gas feed lines, hose lines and connection elements, which can be combined under a generic term of gas guide elements, is therefore of great significance.

Especially in the case of already existing plants or installations of gas-measuring systems with a plurality of gas sensors, there is need for testing the operational capability of the plant during the operation on a regular basis. In particular, there is need, in addition to the testing of the gas sensors, for also testing lines and gas feed lines. For installation situations in which the quantities of gas to be analyzed are fed to the gas sensors from locations located at a distance from the site of installation of the gas sensors by means of gas feed lines, it is advantageous to test the operational readiness and/or operational capability of the gas feed lines as well.

SUMMARY OF THE INVENTION

With the knowledge of the above-described known state of the art and analysis of the drawbacks of the known state of the art, an object of the present invention is therefore to provide a device that makes possible a test of operational capabilities of gas feed lines in a gas-measuring system.

The testing device according to the present invention is for testing a gas guide element in a gas-measuring system that has the gas guide element, a pumping device and at least one gas sensor. The device according to the invention comprises a test gas source and a control unit with connections to the pumping device and at least one gas sensor of the sensor.

The terms measured gas, test gas, scavenging gas and resetting gas used within the framework of this document will be explained in more detail at the beginning.

A measured gas is defined as a gas or a gas mixture that is such that the at least one gas sensor in the gas-measuring system is sensitive to changes in a gas concentration of this measured gas and responds with changes in the gas concentration measured value to changes in a gas concentration of this measured gas.

A scavenging gas or a resetting gas is defined as a gas or gas mixture that is such that the at least one gas sensor in the gas-measuring system is not sensitive to changes in the gas concentration of this gas or gas mixture and does not respond with changes in the gas concentration measured value to changes in the gas concentration of this scavenging gas or resetting gas.

A test gas is defined as a gas or a gas mixture that is such that the at least one gas sensor in the gas-measuring system is sensitive to changes in the gas concentration of this gas or gas mixture and responds to changes in the gas concentration of this test gas with changes in the gas concentration measured value. For example, both the measured gas at a known, but noncritical gas concentration and gases of a known gas concentration, which are similar to the measured gas, may be used as test gases.

Possible measured gases and test gases are reviewed in Table 1 below.

TABLE 1

| Gas | Chemical formula/Empirical formula |
| --- | --- |
| Methane | $CH_4$ |
| Propane | $C_3H_8$ |
| Xenon | Xe |
| Carbon dioxide | $CO_2$ |
| Helium | He |
| Dinitrogen monoxide | $N_2O$ (laughing gas) |

It is essential for the present invention that the at least one gas sensor, which is present as an element of the gas sensor system in the gas-measuring system and is used functionally in the gas-measuring system for the measurement task of detecting gas concentrations of the measured gas at a remotely located measuring location, is also used to test the gas guide element.

The at least one gas sensor is used for this during the testing to detect changes in the gas concentration of the test gas by measurement.

The pumping device with a pump, which is arranged in the pumping device or is associated with the pumping device and which carries out the feed of the measured gas from the remotely located measuring location to the at least one gas sensor in cooperation with the gas guide element, is likewise used for the testing of the operational capability of the gas guide element. Two essential components, namely, the at least one gas sensor and the pumping device are thus already present as essential components in the gas-measuring system. The object of the present invention, namely, the testing of the operational capability of the gas guide element in the gas-measuring system, can be accomplished with the features of the present invention in the gas-measuring system, whose basic functions are known, with a modification of the pumping device and with an addition to the control of the pumping device and by including the test gas source.

The components of the gas-measuring system, their functions and their interaction for testing the gas guide element in the gas-measuring system, will be explained in more detail below.

The gas guide element is used for the gas-carrying connection of the at least one gas sensor to the measuring site, which is located remotely in space from this gas sensor or is arranged at a distance. Such a measuring location, which is located remotely in space or is arranged at a distance, is, for example, a measuring location in underground or aboveground storage tanks or silos, main shafts, inspection shafts, boreholes and other or similar measuring locations.

The at least one gas sensor forms a gas sensor system (the gas sensor system comprises one or more sensor) in the gas-measuring system. The gas sensor system is configured and intended for cyclically or continually detecting the gas concentrations of a gas or of a plurality of gases or gas mixtures as a measured gas or measured gases by measuring in a measuring environment by means of the at least one gas sensor and optionally by means of additional gas sensors and to make such one or more gas sensors available for the control unit in the gas-measuring system as gas concentration measured values.

The gas-measuring system is used here to detect and determine gas concentrations as well as to monitor distinctive threshold values derived from the gas concentrations, for example, the so-called "lower explosive limit" (LEL) or toxic limit values, such as the so-called threshold limit value (TLV).

The measuring environment may be formed in this case directly at or close to the location of the gas sensor system for some of the sensors.

The measuring environment may also be formed for at least one gas sensor by the remotely located measuring location, from which measured gas is fed by means of the gas guide element and the pumping device to the at least one gas sensor for detection for the purposes of a qualitative analysis (gas mixture composition) and/or quantitative gas analysis (gas concentration).

The gas guide element may be configured as a flexible hose line or a semiflexible or rigid pipeline system as well as a combination of hose line elements and pipeline elements, so that one-piece as well as multi-piece or multi-part connections may be formed between the remotely located measuring location and the gas-measuring device.

The gas guide element or an array of gas guide elements is arranged between the remotely located measuring location, the pumping device and the at least one gas sensor (the gas sensor system).

The gas guide element, the at least one gas sensor and the pumping device are connected to one another fluidically and are configured for an interaction such that a quantity of gas can be fed to the at least one gas sensor from the remotely located measuring location and a quantity of gas can be fed from the pumping device to the remotely located measuring location.

The test gas source is arranged at the pumping device and the gas guide element, the at least one gas sensor and the pumping device are connected fluidically such that test gas can be fed as a quantity of gas from the test gas source to the remotely located measuring location. The test gas source may also be configured as a part of the pumping device, and the pumping device may likewise be configured as a part of the test gas source.

The control unit is configured to receive measured values, which are detected and provided by the at least one gas sensor and which indicate a gas concentration. The control unit is further configured by means of a memory, which is associated with the control unit and is arranged in or at the control unit, to store the measured values detected and provided by the at least one gas sensor. In addition, the control unit is configured to coordinate the pumping device in interaction with the at least one gas sensor by means of a sequence of steps in order to test the operational capability of the gas guide element and to determine an indicator of the operational capability of the gas guide element.

The control unit may be configured in the device with the pumping device for testing the operational capability of a gas guide element of a gas-measuring system according to the present invention as an independent unit as well as an element of the pumping device, of the test gas source or of the gas sensor system.

The control unit may further be configured as a distributed control, configured, for example, as a combination of different computers ($\mu P$, $\mu C$) in the gas-measuring system, distributed, for example, among the pumping device, the test gas source, an independent calculation and control unit, as well as part of the gas sensor system.

The operational capability of the gas guide element is tested by means of the control unit, which controls or regulates the pumping device and actuators, preferably pumps, pump drives, diaphragm pumps, piezo pumps, reciprocating pumps, compressor pumps and switching elements, preferably valves, solenoid valves, electromagnetic valves, 2/2-way valves, 2/3-way valves, which are arranged in or at the pumping device or are associated with the pumping device and are suitable for delivering gas, in terms of the functions of the pumping device, namely, delivery pressure, flow rates with direction and quantities and duration of delivery, including suitable sensor systems (pressure, flow, temperature, humidity), which are arranged at the pumping device or are associated with the pumping device.

Measured values provided by the at least one gas sensor are used by the control unit in a testing procedure for testing the operational capability of the gas guide element.

In the course of the testing procedure for testing the operational capability of the gas guide element, the control unit carries out a sequence of steps, in the course of which a quantity of test gas is delivered by means of the pumping device from or out of the pumping device to the remotely located measuring location and is subsequently delivered again from the remotely located measuring location back to the pumping device to the at least one gas sensor.

The control unit performs the following sequence of steps for this:

In a first step, the control unit brings the pumping device into a first operating state for a first, predefined time period. A quantity of test gas is delivered in the first operating state from the test gas source to a remotely located measuring location by means of the gas guide element.

The duration of the first predefined time period is configured by the control unit on the basis of technical properties of the gas guide element and on the basis of technical properties of the pumping device such that the gas guide element is filled with the test gas over a length from the remotely located measuring location to the pumping device. The gas guide element is thus filled completely with the test gas with a total gas volume of the gas guide element over a length from the remotely located measuring location to the pumping device. The technical properties of the pumping device comprise essentially the characteristics of the actuators (pumps) and switching elements (valves) arranged in the pumping device, such as flow rate and pressurized dispensing ranges, which the pumping device provides for delivering the quantity (delivery rate) of test gas from the test gas source by means of the gas guide element to the remotely located measuring location in the first operating state. Furthermore, the technical properties of the pumping device also comprise the type of arrangement of the test gas source at the pumping device, i.e., dimensions, such as length and flow cross section of a partial section of the gas guide element arranged and intended therefor. The technical properties of the gas guide element comprise here dimensions, such as an overall length from the pumping device and/or the at least one gas sensor to the remotely located measuring location, a line diameter belonging to the overall length of the gas guide element, so that a total gas volume present in the gas guide element can be determined from this by the control unit. However, the technical properties of the gas guide element may also comprise the technical properties of individual parts of the gas guide element, i.e., flow cross sections and lengths of different line sections of the gas guide element, in case of a multipart gas guide element. In addition, information on the material, wall thickness, geometric shape (round, elliptical, square), as well as information on a difference in level between the remotely located measuring location and the pumping device or the at least one gas sensor may also be included in the technical properties of the gas guide element. Knowing the technical properties of the individual parts of the gas guide element, the control unit is able to also determine the total gas volume of the multipart gas guide element. The predefined time period so that a quantity of test gas is delivered from the test gas source to the gas guide element in the direction toward the remotely located measuring location may advantageously be based on the at least one or more of the technical properties as comprising at least flow rate of the pump, line length and flow cross section/line diameter.

The first predefined time period is selected by the control unit such that the quantity of test gas delivered by the pumping device into the gas guide element to the remotely located measuring location at the flow rate arising from the technical properties of the pumping device fills the entire gas volume of the gas guide element during the first predefined time period. If, for example, the gas guide element has a gas volume of 5 L over the length of the gas guide element between the pumping device and the remotely located measuring location, the gas guide element is completely filled with the test gas between the pumping device and the remotely located measuring location at a set delivery rate of 0.5 L per minute, which is provided by the pumping device, after a duration of 10 minutes, the gas volume in a partial gas guide element, which connects the test gas source with the pumping device, being ignored in this simplified example.

The pumping device is put by the control unit into a second operating state for a second predefined time period. A quantity of gas is delivered in the second operating state from the remotely located measuring location to the at least one gas sensor in the gas-measuring system by means of the gas guide element.

The duration of the second predefined time period is selected by the control unit on the basis of the first predefined time period and on the basis of technical properties of the gas guide element and/or on the basis of technical properties of the pumping device. The technical properties of the pumping device comprise characteristics of the actuators (pumps) and switching elements (valves) arranged in the pumping device, such as flow rate and pressurized dispensing ranges, which the pumping device provides for delivering the quantity of gas (delivery rate) from the remotely located measuring side of the gas guide element in the second operating state. In addition, the technical properties of the pumping device also comprise the type of arrangement of the at least one gas sensor at the pumping device, i.e., dimensions, such as length and flow cross section of a section of the gas guide element, which is arranged and intended for this. In one constellation, in which the technical properties of the pumping device are nearly identical for the delivery rate from the remotely located measuring location to the pumping device and for the direction of delivery from the test gas source to the remotely located measuring location because, for example, the same pump is used with switchover of the direction of delivery by means of a device comprising two 3/2-way valves coupled by the control unit in the control, the second predefined time period nearly corresponds to the first predefined time period if switchover times of the valves and the duration needed for the delivery of gas by the pumping device to the at least one gas sensor is ignored. If, for example, the gas guide element has a gas volume of 5 L over the length of the gas guide element between the remotely located measuring location and the pumping device, the gas guide element is completely filled with gas between the remotely located measuring location and the pumping device in case of a delivery rate of 0.25 L per minute, which is set and provided by the pumping device, after a duration of 20 minutes. In order for the gas being delivered from the remotely located measuring location to be able to reach the at least one gas sensor, the delivery of the gas must be continued for an additional time period, which is, however, comparatively short compared to the second predefined time period, and the gas volume in a gas guide element, which connects the at least one gas sensor to the pumping device, must additionally also be taken into account during this additional time period. The duration of the second predefined time period thus also comprises the duration that is necessary for the delivery of the gas volume in the gas guide element, which connects the at least one gas sensor to the pumping device, from the pumping device to the at least one gas sensor at a set delivery rate. If the gas volume in the gas guide element, which connects the at least one gas sensor with the pumping device, has a volume of, for example, 0.05 L, an additional time period of ⅕ minute, i.e., 12 sec, is also to be taken additionally into account in the second predefined time period at a set delivery rate of 0.25 L per minute, which is provided by the pumping device.

The control unit receives a plurality of measured values provided by the at least one gas sensor during the second predefined time period. The control unit stores a then current measured value of the provided measured values as a first comparison data value in the memory in the second step at the beginning of the second predefined time period. The control unit stores an additional, then current measured value of the provided measured values as a second comparison data value in the memory in the second step at the end of the second predefined time period.

In a third step, the control unit performs a comparison between the first comparison data value and the second comparison data value and determines an indicator of the operational capability of the gas guide element on the basis of the comparison between the first comparison data value and the second comparison data value and of a predefined comparison criterion. Based on this comparison, the control unit can determine whether the quantity of test gas delivered to the remotely located measuring location in the first operating state has been delivered as a quantity of gas from the remotely located measuring location to the at least one gas sensor in the second operating state. If the first comparison data value and the second comparison data value show hardly any deviations from one another, the result of the comparison is that the quantity of test gas delivered to the remotely located measuring location is identical in terms of volume to the quantity of gas that has been delivered from the remotely located measuring location to the at least one gas sensor.

In such a case, as a basis for the indicator of the functional capability of the gas guide element, the result is that the gas guide element is classified by the control unit as being capable of operating, i.e., there are no significant leaks or leakages over the entire length of the gas guide element from the remotely located measuring location to the at least one gas sensor.

If the second comparison data value is different from the first comparison data value when the predefined comparison criterion is applied, the situation arises in which the gas guide element is not capable of operation, i.e., leaks are present.

The predefined comparison criterion may be configured such that the indicator of the operational capability of the gas guide element is put into the "capable of operating" state if it is found as a result of the comparison between the first comparison data value and the second comparison data value that the difference in the gas concentration between the first comparison data value and the second comparison data value is lower than a predefined difference, for example, <5%.

Depending on the configuration of the gas-measuring system and the complexity of the arrangement of the gas guide elements and connection elements, a range of 0.01% to 10% may be practicable as a difference in the gas concentration for the testing of the operational capability of the gas guide element as a predefined comparison criterion.

In a fourth step, the control unit determines on the basis of the indicator of the operational capability of the gas guide element an output signal, which indicates the indicator of the operational capability of the gas guide element and provides this output signal.

In a preferred embodiment, a scavenging gas source is arranged at the pumping device. The scavenging gas source is arranged at the pumping device and the gas guide element, the at least one gas sensor and the pumping device are connected to one another fluidically such that a quantity of scavenging gas can be fed as a quantity of gas to the at least one gas sensor from the scavenging gas source.

In the first operating state, before the control unit puts the pumping device into the first operating state, in which the quantity of test gas is delivered from the test gas source to the remotely located measuring location by means of the gas guide element, for the first predefined time period in the first step, the control unit is put by the control unit into an expanded operating state for a first predefined time period. A quantity of scavenging gas is delivered in the expanded operating state from the scavenging gas source to the remotely located measuring location by means of the gas guide element, so that the gas guide element is completely filled with the scavenging gas over the length from the remotely located measuring location to the pumping device.

The expanded operating state also corresponds here in the configuration of the predefined time period to the first operating state of the device according to the present invention with a pumping device for testing the operational capability of a gas guide element of a gas-measuring system. The first predefined time period in this expanded operating state may also be called a scavenging time period. This scavenging time period is selected by the control unit such that the delivered quantity of scavenging gas fills the entire gas volume of the gas guide element during the scavenging time period with the set flow rate or delivery rate.

In a preferred embodiment of the device, the test gas source and/or the scavenging gas source is configured as a configuration of a container in combination with an array of valves, switching devices or piezo dispensing elements. The valves, switching devices or piezo dispensing elements can be activated by the control unit by means of control signals such that the test gas and/or the scavenging gas are provided for, sent or fed to the pumping device.

The test gas being stored in the test gas source is preferably the measured gas, which can be detected with the at least one gas sensor, or a gas, to which the gas sensor also responds, in addition to the measured gas, with a change in the gas concentration valve. The use of the measured gas in a known concentration as a test gas for testing the operational capability of the gas guide element offers the advantage that the gas sensor can likewise test in the operational capability, so that testing of the interaction of the components, such as gas guide element, pumping device, gas sensor and test gas source is made possible in the gas guide element.

In a preferred embodiment of the device, the pumping device is configured with a bidirectional pump. The direction of delivery of this bidirectionally delivering pump can be reversed by the control unit by means of a control signal such that either a quantity of measured gas is delivered from the remotely located measuring location to the pumping device and to the at least one gas sensor, or a quantity of test gas is delivered from the test gas source to the remotely located measuring location. The direction of delivery is preferably reversed, for example, directly by means of a reversal of the direction of rotation of the pump motor by the control unit. Such a direct reversal of the direction of delivery by means of the pump has the advantage that only a single pump is necessary without the need for additional arrays of valves in the device for testing the operational capability of the gas guide element.

In another preferred embodiment of the device, the pumping device is equipped with a pump, whose direction of delivery can be set indirectly by means of an array of two so-called 3/2-way valves by the control unit by means of control signals. Respective states of flow of the two 3/2-way valves can be set by the control unit by means of the control signals such that either a quantity of gas is delivered from the remotely located measuring location to the pumping device or to the at least one gas sensor, or a quantity of gas is delivered from the test gas source to the remotely located measuring location.

Such a reversal of the direction of delivery by means of the valve array has the advantage that only one, comparatively simple pump with a permanently preset possible direction of delivery is necessary. In addition, the array of valves ensures that the flow directions within the pumping device, as well as in the gas guide element to the gas sensor and from and to the remotely located measuring location are also defined without an actuation by the control unit by the resting position of the valves. This makes possible a reliable operation of the pumping device in a simple manner without complicated monitoring of the pump and the operation thereof, such as, for example, the direction of delivery of the pump.

In a preferred embodiment of the device, the pumping device is equipped with an array of two pumps arranged in an antiparallel arrangement. The control unit can bring about a mutual activation of one pump or the other by means of a control signal and thus reverse the direction of delivery in the pumping device such that either a quantity of measured gas is delivered from the remotely located measuring location to the pumping device or to the at least one gas sensor, or a quantity of test gas is delivered from the test gas source to the remotely located measuring location. Such a reversal of the direction of delivery by means of two pumps has the advantage that only one pump must be activated by the control unit, so that the directions of delivery can be reversed by the control unit smoothly, without switchover times having to be taken into account as well.

In a preferred embodiment of the device, an additional gas sensor is arranged in addition to the at least one gas sensor. The additional gas sensor is connected fluidically to the pumping device such that a quantity of gas can be fed to the additional gas sensor from the remotely located measuring location. One of the two gas sensors is configured such that it is sensitive to changes in the gas concentration of the measured gas and responds to changes in the gas concentration of the measured gas with changes in the gas concentration measured values. The other of the two gas sensors is configured here such that it is sensitive to changes in the gas concentration of the test gas and responds to changes in the gas concentration of the test gas with changes in the gas concentration measured value.

In a preferred embodiment, a 3/2-way valve is arranged in the device between the pumping device and the at least one gas sensor and the additional gas sensor. A state of flow of the 3/2-way valve can be set by means of a control signal by the control unit such that delivery of the quantity of gas from the remotely located measuring location to the at least one gas sensor or delivery of the quantity of gas from the remotely located measuring location to the additional gas sensor is possible.

Such a configuration with two gas sensors has the advantage that the test gas is not admitted to the at least one gas sensor, which is configured to detect the measured gas, for testing the operational capability of the gas guide element, but a gas different from the measured gas is used as the test gas, which is detected by the additional gas sensor. As a result of this, this gas sensor is again ready for use for the measurement immediately after the testing of the operational capability of the gas guide element. The measured gas is not admitted to this gas sensor for testing purposes, so that this gas sensor also has no waiting time or recovery time. Another advantage of this is that the additional gas sensor provided in this embodiment for testing the operational capability of the gas guide element can be used in a range of markedly higher gas concentrations of the test gas than when the gas sensor must be configured for concentration measurements of both the measured gas, usually in the highest single-digit percentage range (%), but mostly in the promille range (ppm) or even below the promille range (<ppm, ppb), as well as of the test gas. It is thus possible to use a combination of a suitable test gas with a higher gas concentration and of an additional gas sensor adapted to this gas concentration, which combination does not have to be selected as a function of the properties of the measured gas. Gases that are not combustible, explosive and corrosive and are also harmless to health in case of such a use can and should preferably be selected here as the test gas in combination with the additional gas sensor. Nitrogen, carbon dioxide or dinitrogen monoxide shall be mentioned as examples here.

In a preferred embodiment of the device, a gas outlet is arranged in the device, and a 3/2-way valve, whose state of flow can be set by the control unit by means of a control signal such that delivery of the quantity of gas from the remotely located measuring location to the at least one gas sensor or a delivery of the quantity of gas from the remotely located measuring location into the gas outlet is possible, is arranged in the pumping device. The arrangement of the gas outlet with the associated 3/2-way valve offers, for example, the advantage that scavenging of the pumping device as well as of the gas guide element with the gas can be carried out without the scavenging gas having to be fed to the at least one gas sensor. This offers the advantage that the at least one gas sensor has no waiting times or recovery times for detecting the measured gas in the further course of the measuring operation by the at least one gas sensor after the scavenging of the gas guide element. Another advantage of the 3/2-way valve and the gas sensor arises from the fact that the at least one gas sensor can be uncoupled from scavenging gas, measured gas or test gas by the control unit by means of the control signal at any time during the testing of the operational capability of the gas guide element, so that testing, resetting, adjustment (offset, characteristic) or calibration of the at least one gas sensor can be carried out or prompted by the control unit also during the ongoing testing of the operational capability of the gas guide element.

In a preferred embodiment, a 2/2-way valve, whose state is controlled by the control unit by means of a control signal such that test gas or scavenging gas is delivered as a quantity of gas to the remotely located measuring location and no test gas and no scavenging gas is delivered or can reach directly from the test gas source or the pumping device to the at least one gas sensor, arranged in or at the pumping device, the test gas source or the scavenging gas source. The control unit is thus able to ensure in all cases when and for what time period the test gas or the scavenging gas can reach the remotely located measuring location from the test gas source or from the pumping device. This ensures that no undefined gas mixtures are present in the gas guide element even if pumps, which are not activated, are not closed completely against the direction of delivery.

A gas generator is arranged as a test gas source at the pumping device in a preferred embodiment of the device. The gas generator is activated by the control unit by means of a control signal and generates test gas electrolytically, chemically or electrochemically. For example, hydrocarbons, e.g., ethane, can be produced with gas generators.

In a preferred embodiment, the test gas source is configured as a pressure tank, in which the test gas is stored under an admission pressure in the liquid form and is provided for delivery to the remotely located measuring location. A shut-off valve, usually configured as a 2/2-way valve, which is activated by the control unit to allow the test gas being stored under admission pressure in the liquid form to flow into the gas guide element, is arranged in the pumping device. Pressure release occurs during the inflow, so that the test gas flows in the gaseous form into the gas guide element. Suitable test gases for being stored under pressure are, for example, propane, butane, propane/butane mixtures. In a configuration with a test gas that is under an admission pressure, a pump is not necessary in all applications for delivering the test gas to the remotely located measuring location in the device for testing the operational capability of the gas guide element. A pump is necessary only when a greater distance must be covered from the pumping device to the remotely located measuring location for delivering the test gas to the remotely located measuring location or when a greater level difference must be overcome from the pumping device to the remotely located measuring location, whether the remotely located measuring location is located at a markedly higher elevation than the pumping device or the test gas source or the remotely located measuring location is located at a markedly lower elevation than the pumping device or the test gas source. This happens, for example, in applications in which the distance—and hence the length of the gas guide element—is greater than 15 m or a difference greater than 10 m in elevation must be overcome. The delivery of the test gas to the remotely located measuring location is otherwise brought about and made possible by the admission pressure of the test gas as an inflow on the basis of the pressure difference between the pressure tank and the measuring location. The control unit can thus bring about the flow to the remotely located measuring location by means of activation of the shut-off valve (2/2-way valve) by a control signal.

The pump or pumps described in the embodiments of the pumping device is/are preferably controlled, for example, in terms of the delivery rate and/or the flow rate and/or the delivery pressure of the pump, via the speed of rotation n of a pump motor provided in or at the pump for driving the pump. The control of the delivery rate, flow rate or delivery pressure is defined in the sense of the present invention as any kind of external influence by means of setting, adjusting, controlling or regulating the pump in terms of its speed of rotation n, the delivery pressure, the flow rate or the delivery rate. An electrically operated pump motor may be controlled by the control unit, for example, according to a speed of rotation characteristic or speed of rotation-flow characteristic by means of control signal configured as a d.c. signal or as a pulse-width modulated signal (PWM).

In a preferred embodiment of the device, a pressure sensor is arranged in or close to the pumping device at the gas guide element. The pressure sensor is configured to detect pressure conditions occurring or prevailing in the gas guide element or pressures of the quantity of test gas or measured gas. The pressure sensor provides the detected pressures as measured values for the control unit. The control unit is configured to control, i.e., set, control or regulate the delivery rate and/or the flow rate and/or the delivery pressure of the pump or pumps in the pumping device on the basis of the measured values.

In a preferred embodiment of the device, a flow sensor is arranged in or close to the pumping device in the gas guide element. The flow sensor is configured to detect flows rates of the quantity of test gas or measured gas flowing in the gas guide element. The flow sensor provides the detected flow rates as measured values for the control unit. The control unit is configured to control, i.e., set, control or regulate the delivery rate and/or the flow rate and/or the delivery pressure of the pump or pumps on the basis of the measured values of the flow.

The embodiments described represent both in themselves and in combination or combinations with one another special embodiments of the device with a pumping device for testing a gas guide element. All and possible additional embodiments and their advantages arising from a combination or combinations of a plurality of embodiments are likewise also covered by the inventive idea, even if not all the combination possibilities of embodiments are specifically described for this in detail.

The present invention will now be described in more detail by means of the following figures and the corresponding description of the figures without limitation of the general inventive features. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1b is a schematic view of a first variant of the pumping device according to FIG. 1a;

FIG. 1c is a schematic view of a second variant of the pumping device according to FIG. 1a;

DESCRIPTION OF THE PREFERRED EMBODIMENTS

Figure 1A:
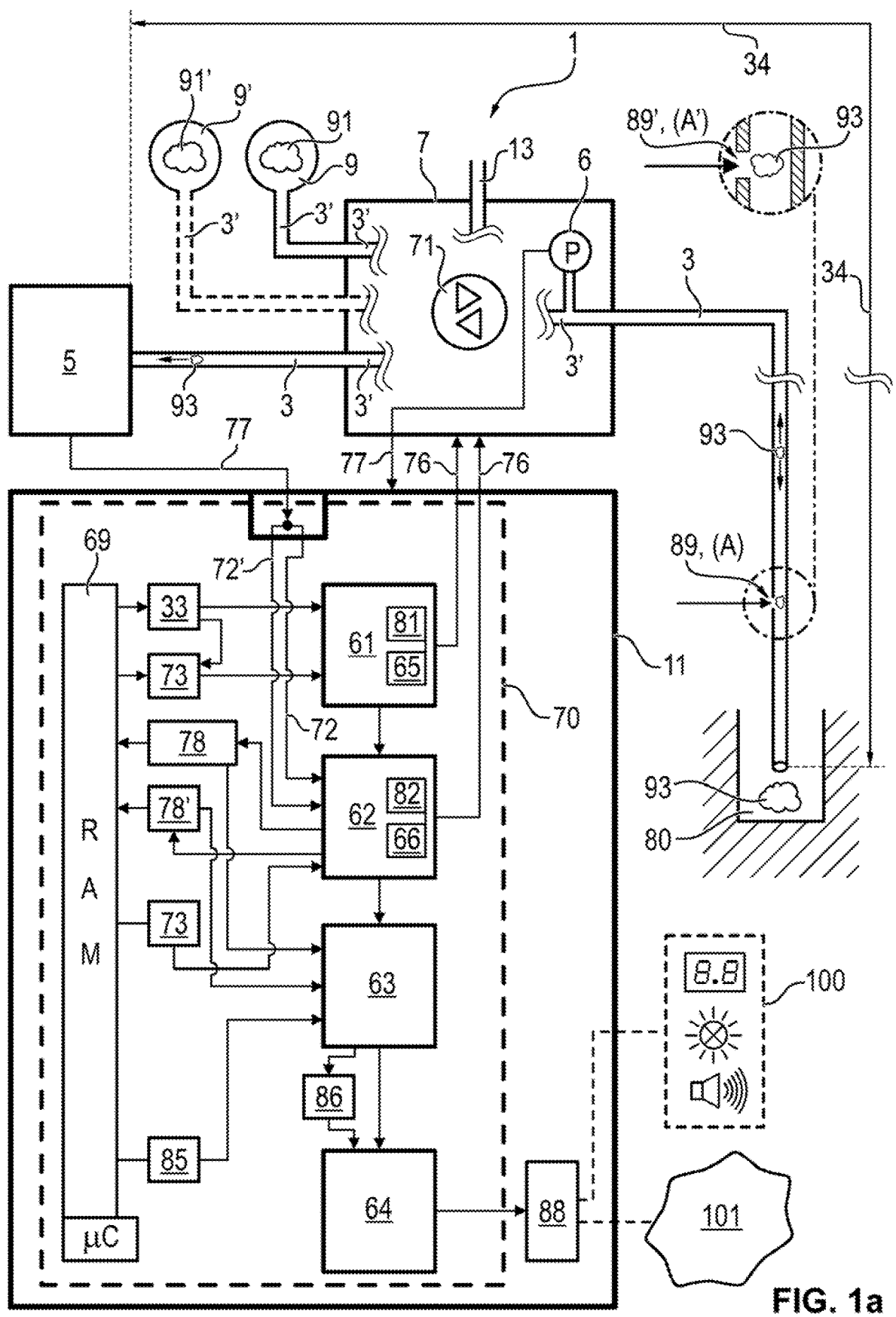
FIG. 1a is a schematic view of a device with a pumping device for testing the operational capability of a gas guide element.

Referring to the drawings, FIG. 1a shows a schematic view of a device 1 with pumping device 7 for testing the operational capability of a gas guide element 3 in a gas-measuring system 11.

The operational capability determination device 1 determines the operational capability of the gas guide element 3 in the gas-measuring system 11. The gas-measuring system 11 has a gas sensor (a gas sensor system comprising one or more gas sensor) 5, a pumping device 7, and the gas guide element 3. The operational capability determination device 1 comprises a test gas source 9 and a control unit 70 with an associated memory 69. The control unit 70 has connections (signal line connections) to the pumping device 7 and the one or more gas sensor 5. The control unit 70 may be a part of the system 11 and may be configured as described below to provide the control features of the operational capability determination device 1. The gas sensor system 5, the pumping device 7, and the gas guide element 3 also provide features of the operational capability determination device 1.

The device 1 for determining the operational capability of the gas guide element 3 is shown in this FIG. 1a in a global context of an application in the gas-measuring system 11. The gas-measuring system 11 has a remotely located measuring location 80, from which gas is delivered via the gas guide element 3 by means of the pumping device 7 to the gas sensor 5. The remotely located measuring location 80 may be, for example, a tank, a silo, a shaft, a tunnel, as well as a tank on a motor vehicle, a tank on a ship or a storage room on a ship. The situation that maintenance personnel must be able to assess the situation concerning a gas concentration that is hazardous to health in such a tank, silo or storage location by means of a measurement is characteristic of the remotely located measuring location 80. A quantity of gas 93 is delivered for this by means of the gas guide element 3 from this tank or silo to the gas sensor 5. It is important for the gas guide element to be able to function, i.e., intact and free from leaks over an entire length 34 from the remotely located measuring location 80 to the gas sensor 5 for this delivery of the quantity of gas 93. The pumping device 7 is therefore configured in the embodiment of FIG. 1a as a part of the system 11, to deliver quantities of gas 93 from the remotely located measuring location 80 to the gas sensor 5, but also as a part of the device 1, to deliver quantities of gas 93 as test gas 91 from the test gas source 9 to the remotely located measuring location 80. The gas guide element 3 is flooded or filled with the test gas during this delivery over the length 34 from the remotely located measuring location 80 into the pumping device 7. The volume of test gas 91, which was just delivered into the gas guide element 3, is delivered back again into the pumping device 7 during the subsequent delivery from the remotely located measuring location 80 and is fed by the pumping device 7 to the pressure sensor 6 for an analysis of changes in the gas concentration over time of the return delivery of the test gas 9. When gas concentration measured values 77 of the gas sensor 5 are then analyzed with the gas sensor 5 at the beginning of the return delivery as well as at the end of the return delivery, operational capability of the gas guide element 3 can be inferred.

If no change occurs in the gas concentration between the measured values, measured at the beginning of the return delivery and the measured values measured at the end of the return delivery, it can be inferred that no leakage or leak, from which a quantity of gas 93 could escape from the gas guide element 3, for example, into the ambient air, is present in the gas guide element 3.

The gas guide element 3 is arranged between the pumping device 7, the gas sensor 5 and the gas sensor 5. The gas guide element 3, the pressure sensor 6, the gas sensor 5, and the pumping device 7 are connected to one another fluidically and configured for an interaction such that a quantity of gas 93 can be fed to the gas sensor 5 from a remotely located measuring location 80 and the quantity of gas 93 can be fed from the pumping device 7 to the remotely located measuring location 80.

A location A 89 of a possible leak is shown on the gas guide element 3 in this FIG. 1a. In addition, the leak A 89 is shown as an enlarged detail A' 89' with the quantity of gas 93 as a leakage (leak) in the wall of the gas guide element 3.

The test gas source 9 is arranged in or at the pumping device 7 and the gas guide element 3, the gas sensor 5 and the pumping device 7 are connected to one another fluidically such that a quantity of test gas 91 can be fed as a quantity of gas 93 to the remotely located measuring location 80 from the test gas source 9.

This FIG. 1a schematically shows in the pumping device 7 a bidirectionally delivering pump 71, which can be activated by means of the control unit 70 for delivering quantities of gas 93 from the pumping device 7 to the remotely located measuring location and from the remotely located measuring location 80 by means of a control signal 76. A detailed description of the pumping device 7 with the bidirectionally delivering pump 71 is contained in the description of FIG. 1c.

Figure 2A:
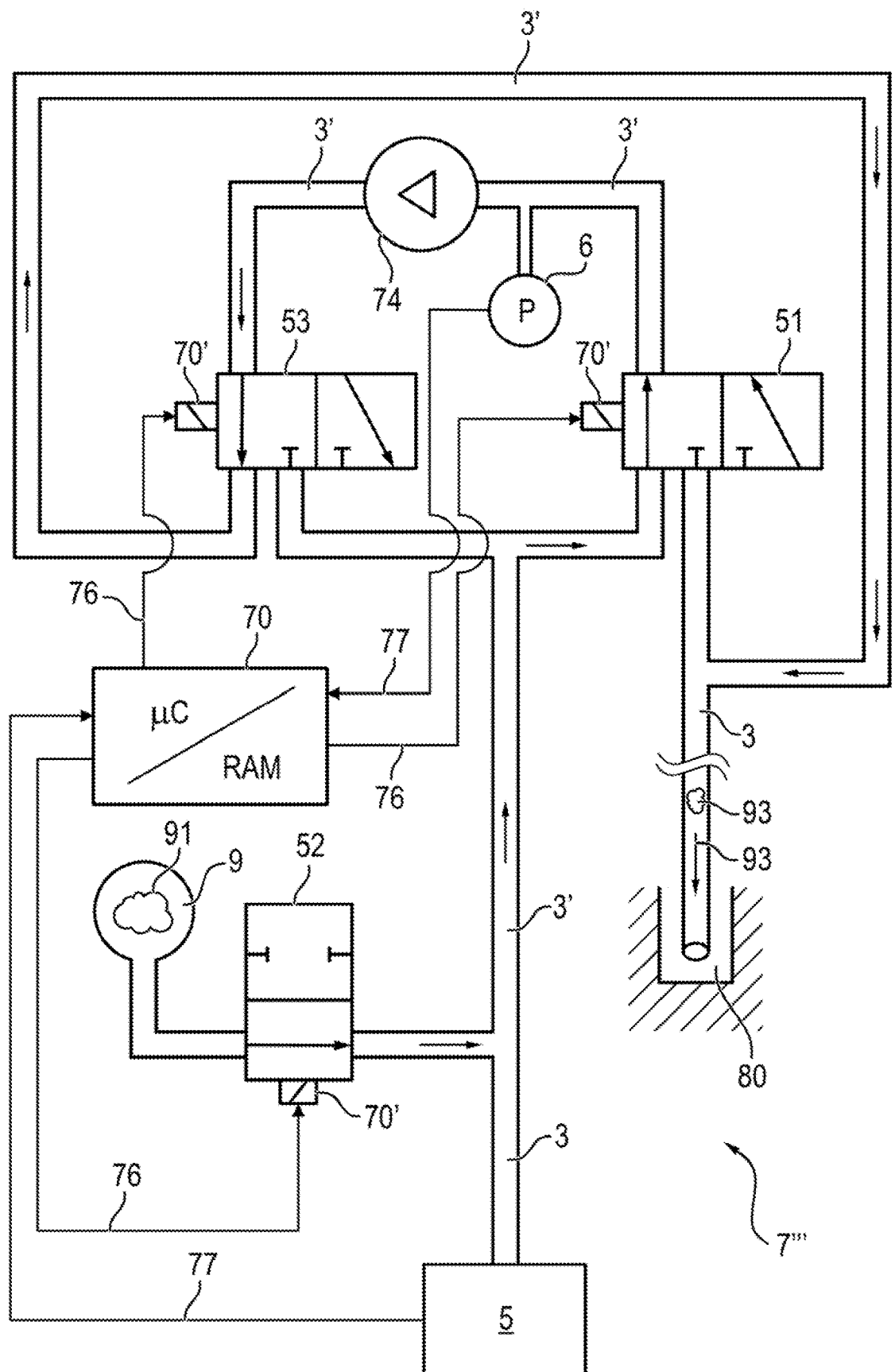
FIG. 2a is a schematic view of a third variant of the pumping device according to FIG. 1a in a first operating state.
Figure 2B:
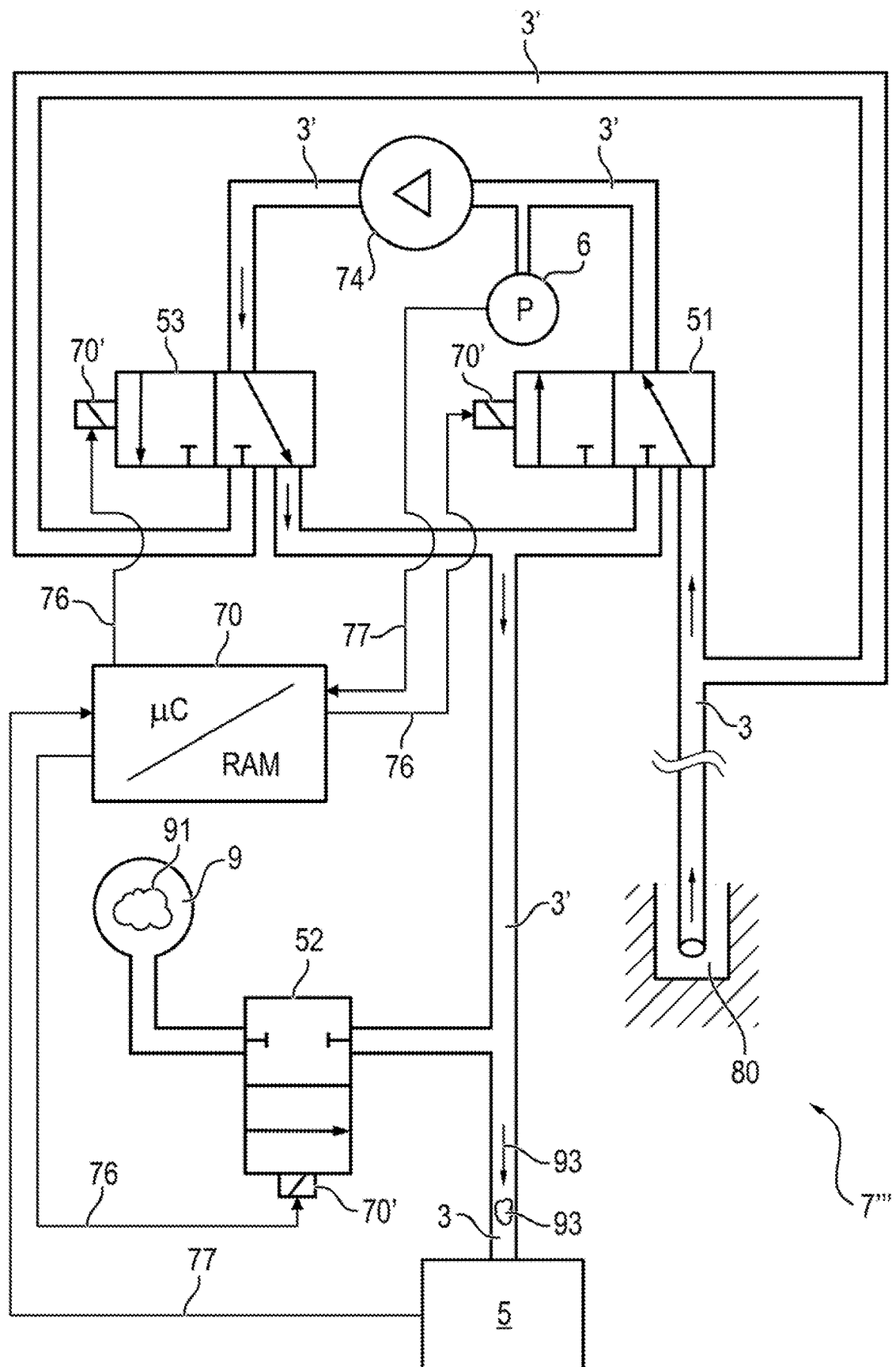
FIG. 2b is a schematic view of the third variant of the pumping device according to FIG. 1a in a second operating state.
Figure 3A:
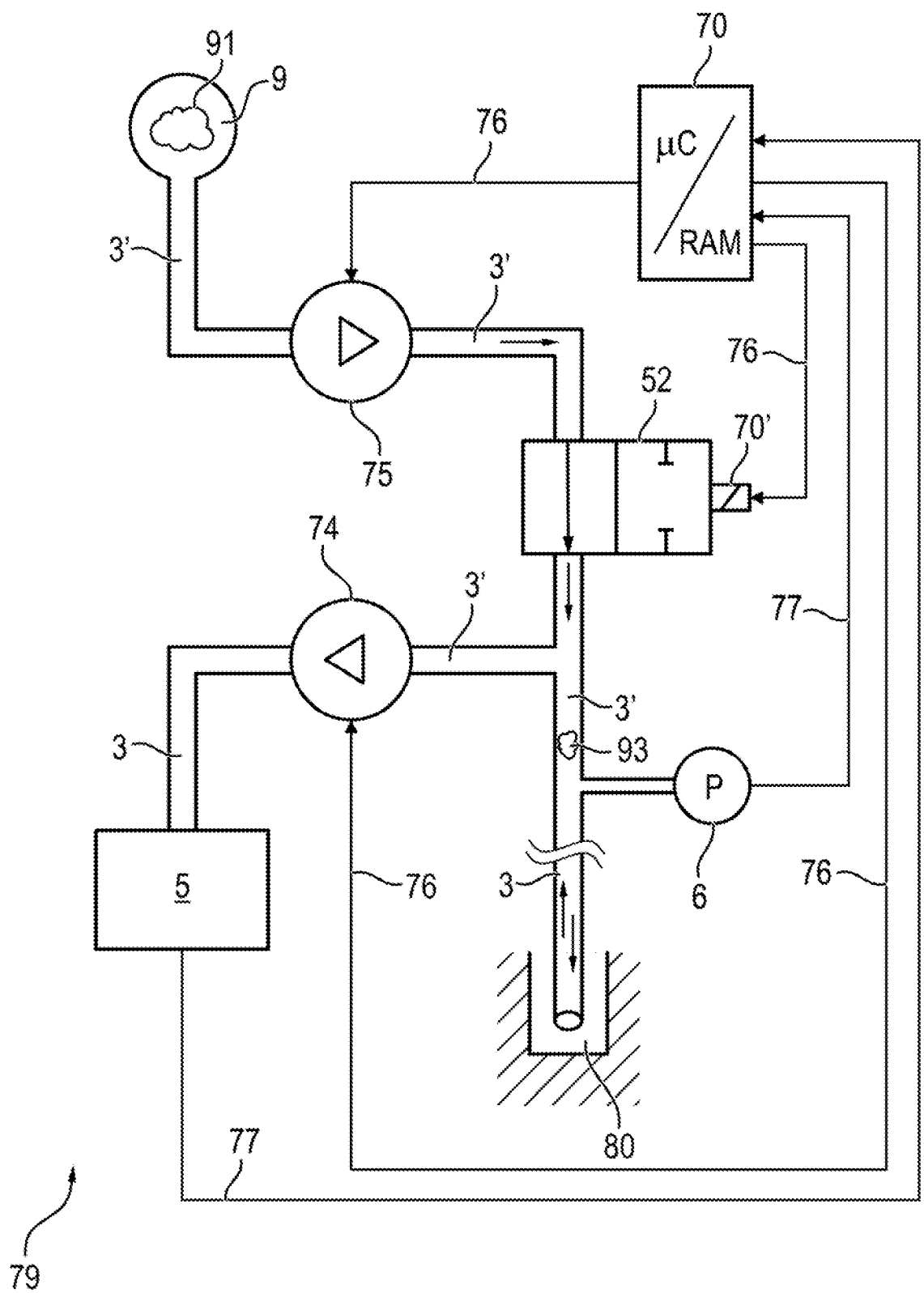
FIG. 3a is a schematic view of a fourth variant of the pumping device according to FIG. 1a in a first operating state.
Figure 3B:
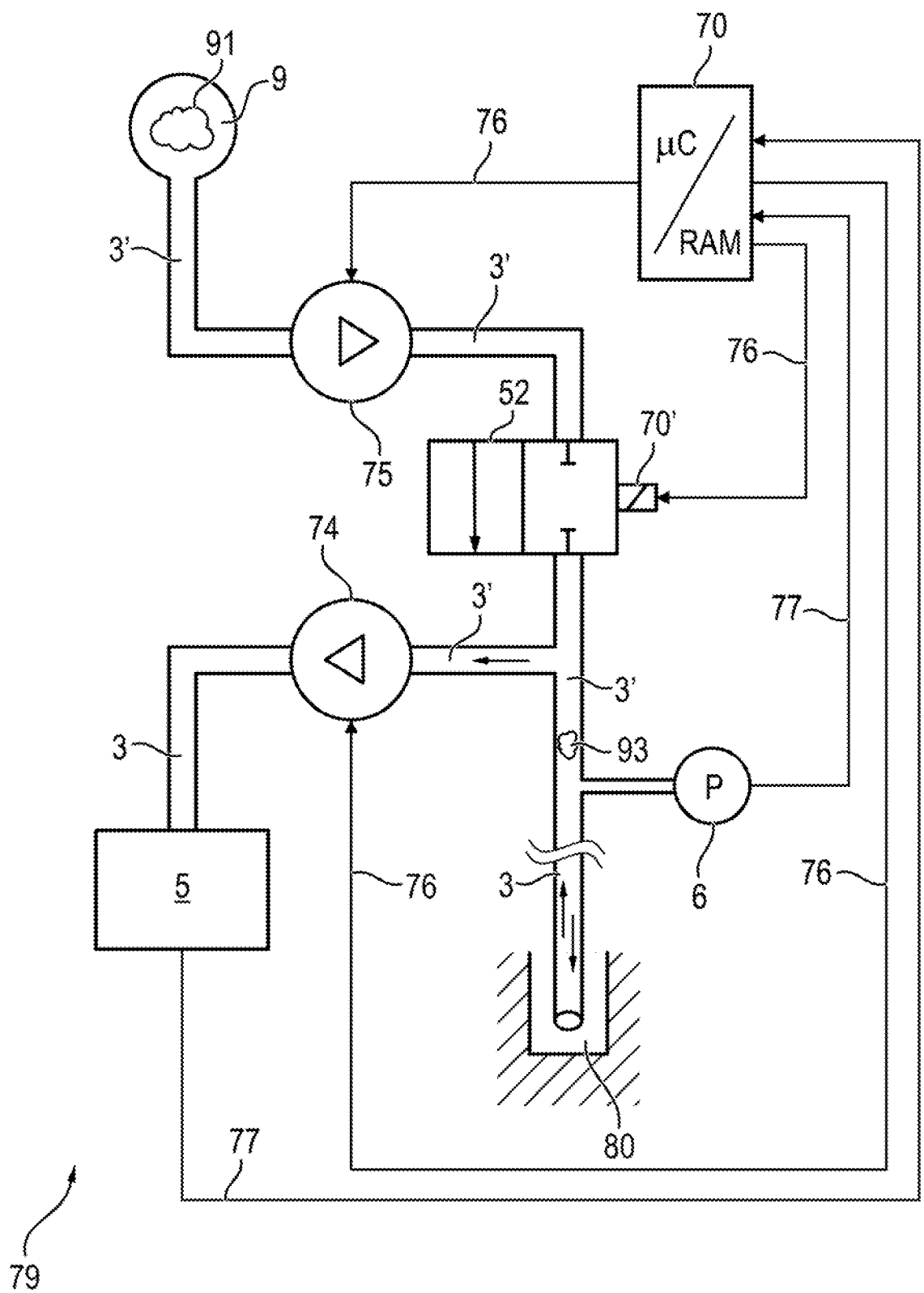
FIG. 3b is a schematic view of the fourth variant of the pumping device according to FIG. 1a in a second operating state.
Figure 4:
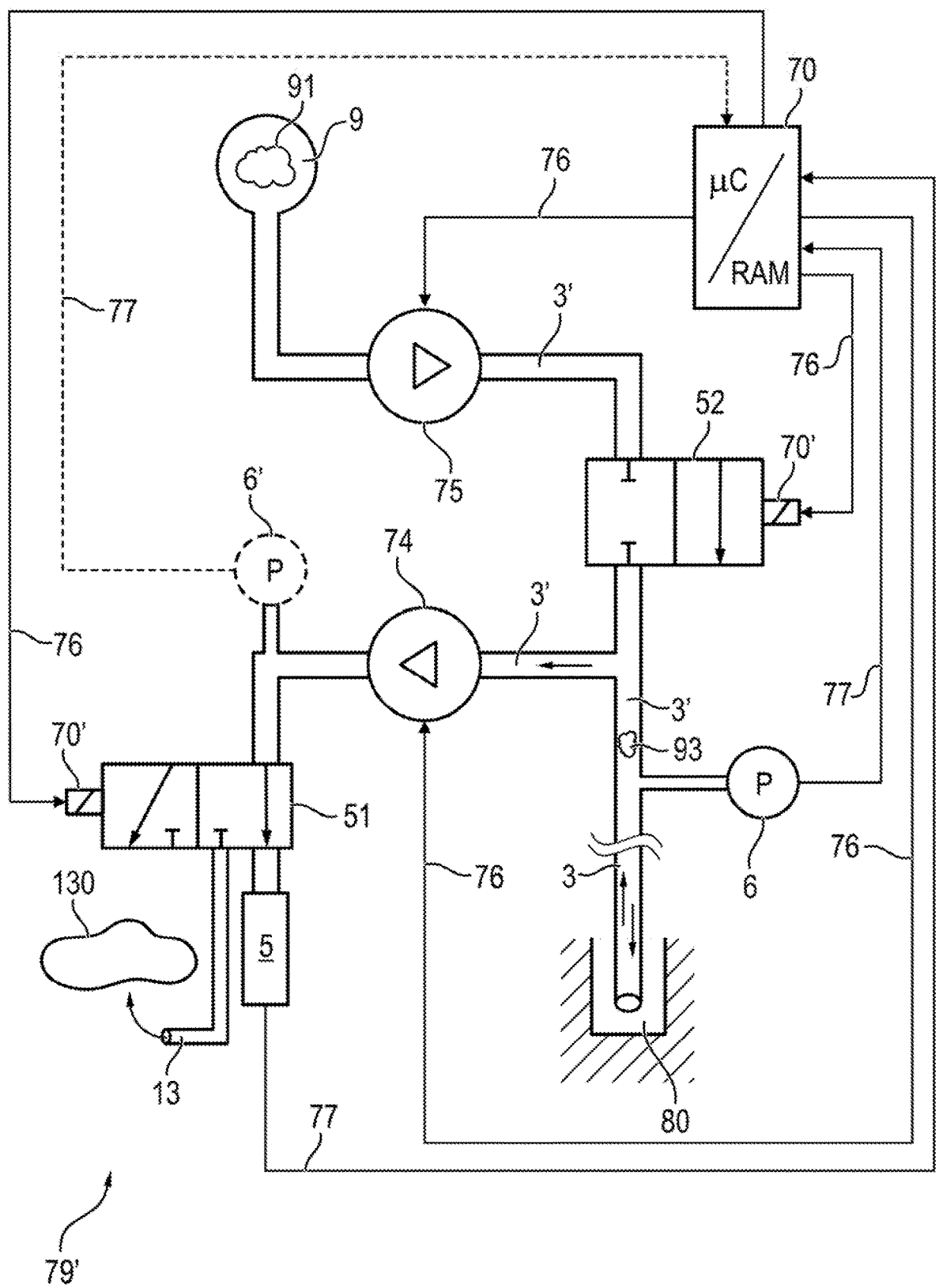
FIG. 4 is a schematic view of a variant of the device according to FIGS. 3a, 3b with a gas outlet.

FIGS. 1b, 1c, 2a, 2b, 3a, 3b, 4 and 5 and the descriptions of FIGS. 1a, 1c, 2b, 2b, 3a, 3b, 4 and 5 describe additional embodiments of the pumping device with variants of pumps 74, 75 (FIGS. 1b, 2a, 2b, 3a, 3b, 4 and 5), arrangements of switching elements 70' (FIGS. 2a, 2b, 3a, 3b, 4 and 5) and pumps 74, 75 (FIGS. 2a, 2b, 3a, 3b and 4), configurations of arrays of valves 51, 52, 53 (FIGS. 1b, 2a, 2b, 3a, 3b, 4 and 5), in addition to other peculiar features of the configuration of the device 1 and of the pumping device 7, 7', 7", 7''', 79, 79', 79" (FIGS. 1a, 1b, 1c, 2a, 2b, 3a, 3b, 4 and 5). The control, activation or control of components 51, 52, 53, 70', 71, 74, 75 (FIGS. 1a, 1b, 1c, 2a, 2b, 3a, 3b, 4 and 5) is carried out in these FIGS. 1b, 1c, 2a, 2b, 3a, 3b, 4 and 5 by the control unit 70 by means of control signals 76. The gas sensor 5 as well as the additional gas sensor 5' (FIG. 5), the pressure sensor 6 (FIG. 1b) for monitoring the pressure of the quantity of gas 93 flowing to the gas sensor, which pressure sensor is indicated in this FIG. 1a as an optional component of the pumping device 7, as well as the additional pressure sensor 6' (FIG. 4) as well as the flow sensor 90 (FIG. 1c) provide measured values 77 for the control unit 70. An optional gas outlet 13, whose mode of action is described in more detail in FIG. 4 and in the description of FIG. 4, is indicated in the pumping device 7 in this FIG. 1a.

Figure 5:
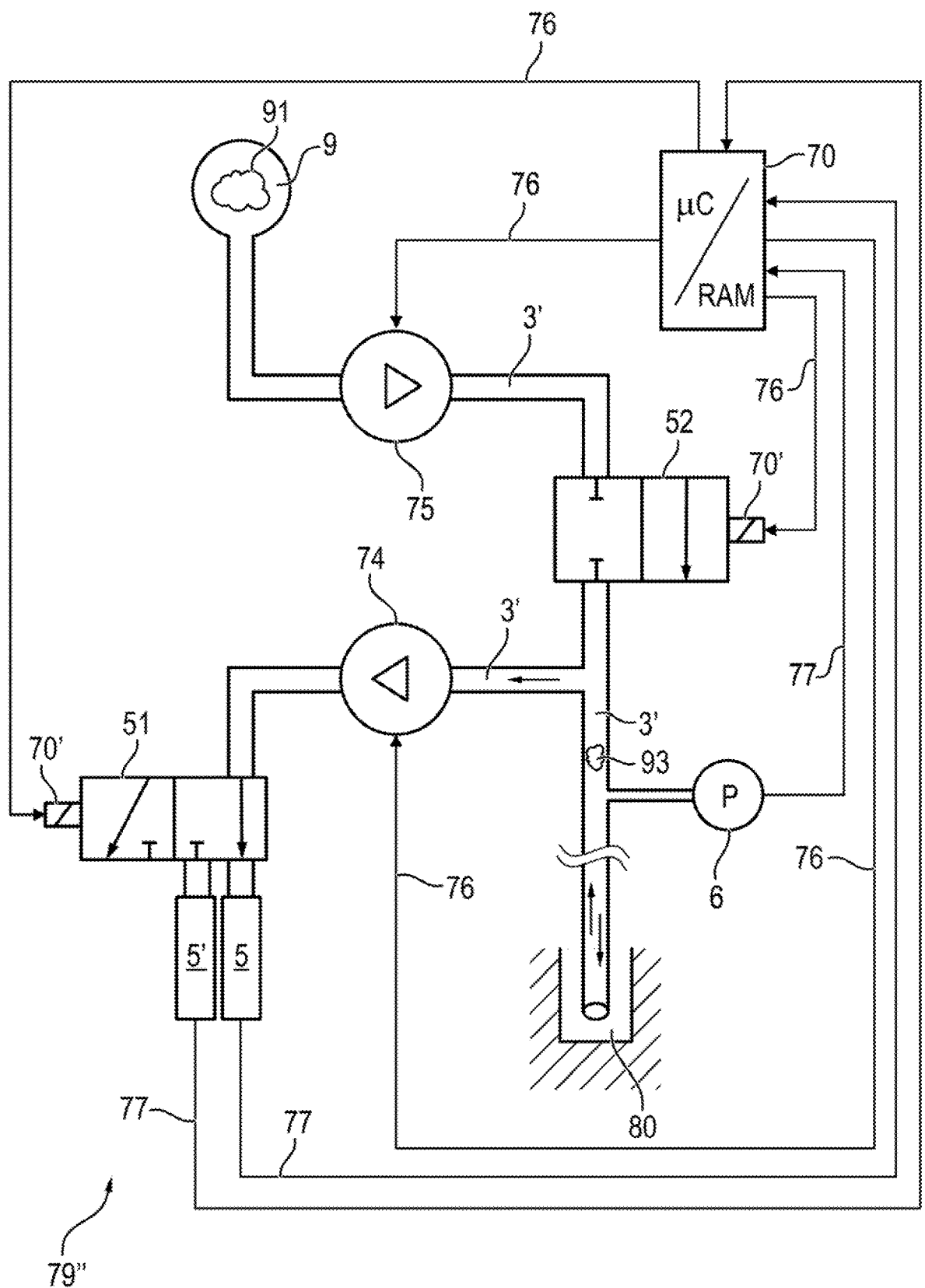
FIG. 5 is a schematic view of a variant of the device according to FIGS. 3a, 3b with an additional gas sensor.

The control unit 70 is configured to carry out the testing of the operational capability of the gas guide element 3 on the basis of the measured values 77 of the gas sensor 5 as well as of the additional gas sensor 5' (FIG. 5). The control unit 70 is further configured to optionally also include measured values 77 of the pressure sensor 6 for the control of the pumping device 7, 7', 7", 7''', 79, 79', 79" and components 51, 52, 53, 70', 71, 74, 75 thereof (FIGS. 1a, 1b, 1c, 2a, 2b, 3a, 3b, 4 and 5).

A plurality of internal gas guide elements 3', which are necessary for the internal connections of the components 6, 71, 9, 9' (FIG. 1a) and 52, 53, 71, 74, 75, 9, 9' (FIGS. 1a, 1b, 1c, 2a, 2b, 3a, 3b, 4 and 5) within the pumping device 7, are provided in the pumping device 7. The separation of the gas guide elements 3 from the internal gas guide elements 3' is not unambiguous, and all gas guide elements 3, 3' rather represent together the necessary fluidic connections between the gas sensor 5, the pumping device 7 and the components thereof and the remotely located measuring location 80. The testing of the operational capability of the gas guide element 3, 3' also takes place together, because a reliable operating state of the gas-measuring system 11 can also only be ensured if all the fluidic connections necessary in the particular measuring application are in an error-free state. In addition to the test gas source 9, an optional scavenging gas source 9' for storing a scavenging gas 91', which is configured and intended for providing scavenging gas 91' for feeding the scavenging gas 91' to the remotely located measuring location 80 by means of the pumping device 7, is also arranged at the pumping device 7. This makes it possible to scavenge the pumping device 7 and the gas guide elements 3, 3' with the scavenging gas 91', for example, to create defined gas states in the components 3, 3', 7, 5, 80, 6, 71 of the device 1 and of the gas-measuring system 11 as boundary conditions for the start of the testing of the operational capability of the gas guide element 3.

As was explained above, the control unit 70 is configured to receive measured values 77, which are detected and provided by the gas sensor 5 and which indicate a gas concentration, and to store the measured values 77 detected and provided by the gas sensor 5 in a memory 69, which is associated with the control unit 70 and is arranged in or at the control unit 70. The control unit 70 carries out the determination of the operational capability of the gas guide element 3 so as to coordinate the interaction of the pumping device 7 with the gas sensor 5 by means of a sequence of steps.

Starting from the measuring operation, the control unit 70 puts the pumping device 7 into a first operating state 65 for a first predefined time period 81 in a first step 61, so that a quantity of test gas 91 is delivered from the test gas source 9 to the remotely located measuring location 80 by means of the gas guide element 3.

The duration of the first predefined time period 81 is configured by the control unit 70 on the basis of technical properties 33 of the gas guide element 3 and on the basis of technical properties 73 of the pumping device 7 such that the gas guide element 3 is filled with the test gas 91 over a length 34 from the remotely located measuring location 80 to the pumping device 7. The technical properties 73 of the pumping device 7 comprise essentially characteristics of the components 51, 52, 53, 71, 74, 75, 9, 9' (FIGS. 1a, 1b, 1c, 2a, 2b, 3a, 3b, 4 and 5) arranged in the pumping device 7, such as flow rate and pressure dispensing ranges, which the pumping device 7 provides for delivering the quantity 93 of test gas 91 from the test gas source 9 to the remotely located measuring location 80 by means of the gas guide element 3 in the first operating state 65. Furthermore, the technical properties 73 of the pumping device 7 also comprise the manner of arrangement of the test gas source 9 at the pumping device 7, i.e., dimensions, such as length 34 and flow cross section of a section of the gas guide element 3, which section is arranged and intended therefor. The technical properties 33 of the gas guide element 3 comprise dimensions, such as an overall length from the pumping device 7 and/or from the gas sensor 5 to the remotely located measuring location 80 and a line diameter belonging to the overall length of the gas guide element 3, so that a total volume of gas present in the gas guide element 3 can be determined from this by the control unit 70. However, the technical properties 33 of the gas guide element 3 may also comprise the technical properties of individual parts of the gas guide element 3, i.e., flow cross sections and lengths 34 of different line sections of the gas guide element 3, in case of a multipart gas guide element 3. In addition, information on the material, wall thickness, geometric shape (round, elliptical, square) as well as information on a difference in level between the remotely located measuring location 80 and the pumping device 7 or the gas sensor 5 may also be comprised in the technical properties 33 of the gas guide element 3. Knowing the technical properties of the individual parts of the gas guide element 3, the control unit 70 is able to also determine the total gas volume of the multipart gas guide element 3.

In a second step 62, the control unit 70 puts the pumping device 7 into a second operating state 66 for a second predefined time period 82, so that a quantity of gas 93 is delivered from the remotely located measuring location 80 to the gas sensor 5 by means of the gas guide element 3. The duration of the second predefined time period 82 is configured by the control unit 70 on the basis of the first predefined time period 81 and on the basis of the technical properties 33 of the gas guide element 3 and on the basis of the technical properties 73 of the pumping device 7. The control unit 70 receives and detects a plurality of measured values 77 provided by the gas sensor 5 during the second predefined time period 82. In the second step 62, the control unit 70 stores in the memory 69 a then current measured value 72 of the provided measured values 77 as a first comparison data value 78 at the beginning of the second predefined time period 82 and a then current measured value 72' of the provided measured values 77 as a second comparison data value 78' at the end of the second predefined time period 82.

In a third step 63, the control unit 70 performs a comparison between the first comparison data value 78 and the second comparison data value 78' and determines an indicator 86 of the operational capability of the gas guide element 3 on the basis of the comparison between the first comparison data value 78 and the second comparison data value 78' and of a predefined comparison criterion 85. The indicator of the operational capability of the gas guide element 3 can be put by the control unit 70 by means of the comparison criterion 85 into the "capable of operating" state if the result of the comparison between the first comparison data value 78 and the second comparison data value 78' shows that the difference in the gas concentration between the first comparison data value 78 and the second comparison data value 78' is lower than a predefined difference between the comparison data values 78, 78'. For example, a difference in the range of <3% to <5% may be utilized. Depending on the configuration of the gas-measuring system 11 and the complexity of the arrangement of gas guide elements 3 and connection elements, a range of 0.01% to 10% may be practicable as a difference in the gas concentration for the testing of the operational capability of the gas guide element 3 as a predefined comparison criterion 85. In case of a small difference between the comparison data values 78, 78', the result of the testing of the operational capability of the gas guide element 3 by the control unit 70 is that the gas concentration in the gas guide element 3 has not changed significantly over the entire length 34 from the remotely located measuring location 80 to the gas sensor 5 during the time period and no leak A 89 is consequently present in the gas guide element 3.

In a fourth step 64, the control unit 70 determines an output signal 88, which indicates the determined indicator 86 for the operational capability of the gas guide element 3 and provides this output signal 88.

FIG. 1a shows an optional output and alarm generation unit 100. The output signal 88 is provided in this configuration with the optional output and alarm generation unit 100 by the control unit 70 to the output and alarm generation unit 100, so that with this it is made possible to output a status on the basis of the determined indicator 86 of the operational capability of the gas guide element 3 or to generate an alarm in case of a leakage situation A 89. The output and alarm generation unit 100 usually has display elements, such as alphanumeric display lines or a graphics display for the output and usually acoustic signal generation elements, such as horns or other sound generators (loudspeakers) for the alarm generation and optical alarm generation elements, for example, blinking lighting devices (incandescent lamps, LED). The output and alarm generation unit 100 may be arranged close by as a part of the gas-measuring system 11 or at another location, not shown in this FIG. 1a, and may be connected to the gas-measuring system 11, for example, as a module or assembly unit of an optional analysis system 101 in a data network.

Figure 1B:
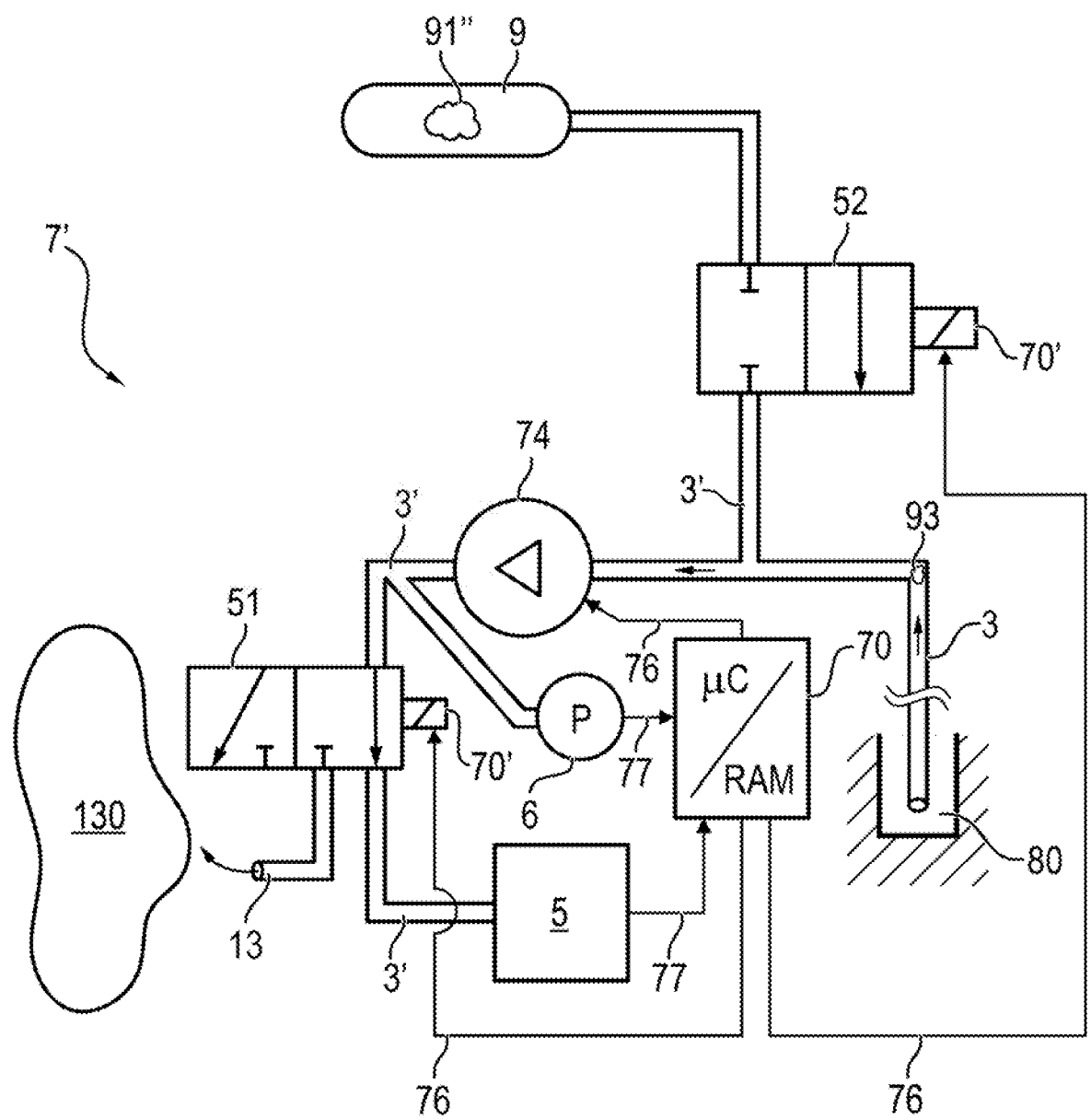

FIG. 1b shows a first variant 7' of the pumping device according to the device 1 shown in FIG. 1a. Identical components in FIGS. 1a, 1b are designated by the same reference numbers in FIGS. 1a, 1b. This variant of the pumping device 7' according to FIG. 1b is based on the device 1 according to FIG. 1a with the test gas source 9, control unit 70, gas outlet 13, gas sensor 5, pressure sensor 6, measured values 77, gas guide elements 3, 3' with fluidic connection to the remotely located measuring location 80. The first variant 7' additionally has a 2/2-way valve 52, a 3/2-way valve 51 and a unidirectionally delivering pump 74.

The test gas source 9 is configured in this FIG. 1b as a pressure tank, in which the test gas 91" is stored in the liquid state under an admission pressure and is provided for delivery to the remotely located measuring location 80. The 2/2-way valve 52, which is activated by the control unit 70 in order to allow the test gas 91" to flow into the gas guide element 3, is arranged in this pumping device 7'. A pressure release takes place during the inflow, so that gaseous test gas 91" will in this case flow into the gas guide element 3. Suitable test gases 91" for storage in the liquid state under pressure are, for example, propane, butane, and propane/butane mixtures.

The 2/2-way valve 52 can be used to avoid a state in which the test gas 91" can directly reach the gas sensor 5 from the test gas source 9 or is delivered by means of the pump 74. By means of a control signal 76, the control unit 70 can activate a switching element 70' in order to open the valve 52, so that the test gas 91" can reach the internal gas guide element 3' for delivery to the pump 74 only during the first operating state 65 (FIG. 1a).

A gas outlet 13, with function and advantages that are also described in more detail in FIG. 4 and in the description of FIG. 4, is arranged in the pumping device 7' in the embodiment of FIG. 1b. Just like the gas sensor 5, the gas outlet 13 is connected in this FIG. 1b to the pump 74 by means of the 3/2-way valve 51. The 3/2-way valve 51 can be put by the control unit 70 into two different states of flow with a control signal 76. This makes possible the delivery of the quantity of gas 93, which is delivered by means of the pump 74 from the remotely located measuring location 80, to the gas sensor 5 or through the gas outlet 13 into a surrounding area 130 or into a gas discharge line.

The pressure sensor 6 is shown in this FIG. 1b as a part of the pumping device 7', which part is configured to detect the measured values of a pressure 77 at the gas guide element 3 and to transmit them to the control unit 70. The control unit 70 is able by means of the measured values of the pressure 77 to control the pump 74 in terms of the delivery pressure and/or the flow rate. For example, a pump motor driving the pump 74 can be controlled or regulated for this by means of characteristics [P=F(n), n=F(U)], with P the pressure a function of speed and speed a function of the control signal U(74). The control of the pump is working with characteristic curves which incorporate dependencies between pressure P and revolution n, where P is a function of n and n is depending from a control signal U (74), provided by the control unit (70) to the pump (70). The control signal U is representing an electrical signal, like a DC- or AC-Voltage (U[V]) or current DC- or AC-Current (I[A]), or a pulse width modulated (Voltage) signal (PWM).

Figure 1C:
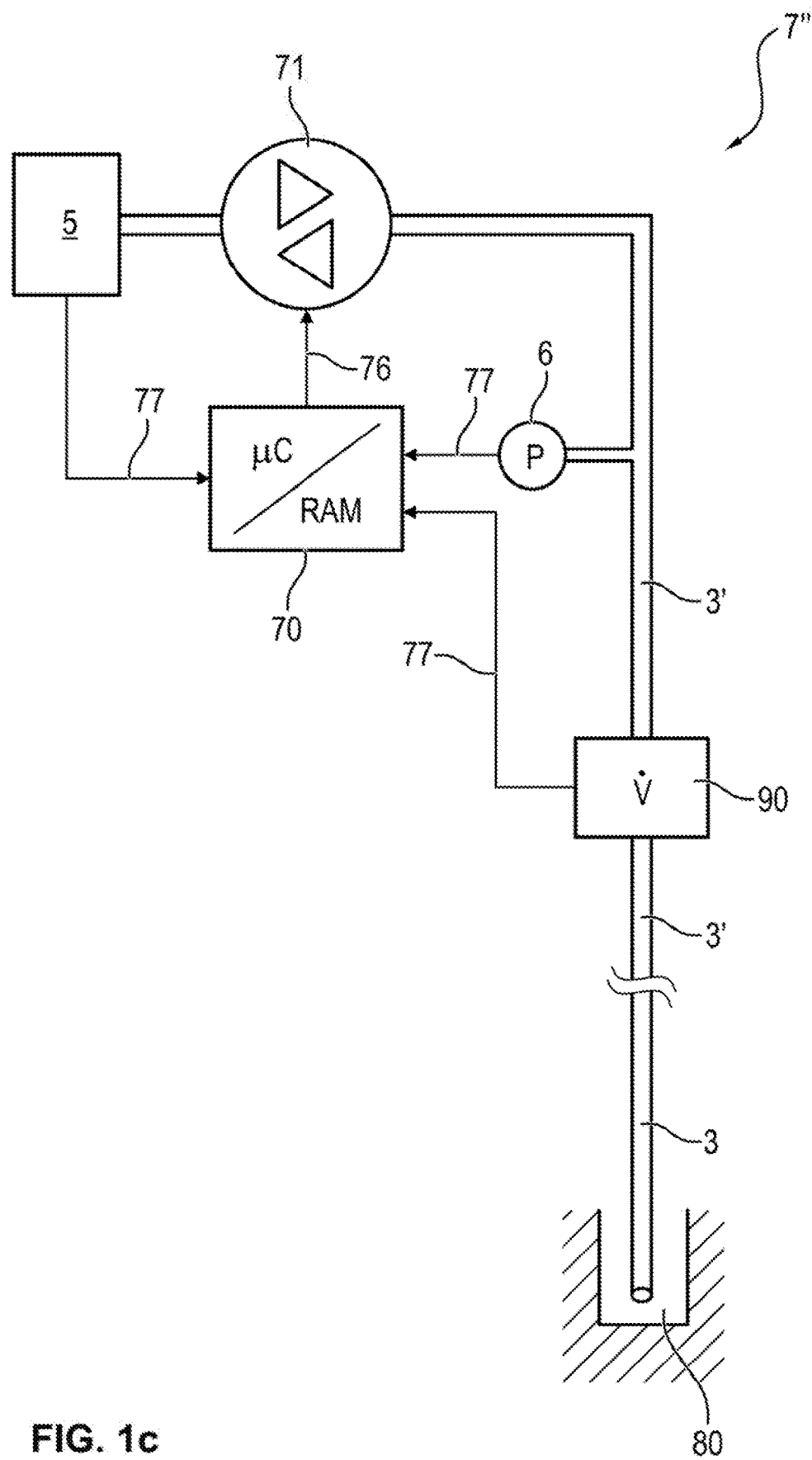

FIG. 1c shows a second variant of the pumping device 7 according to the device 1 shown in FIG. 1a as a pumping device 7". Identical components in FIGS. 1a, 1c are designated by the same reference numbers in FIGS. 1a, 1c. This variant of the pumping device 7" according to this FIG. 1c is based on the device 1 according to FIG. 1a with the control unit 70, control signals 76, gas sensor 5, pressure sensor 6, the measured values 77, the switching elements 70' and the gas guide elements 3, 3' with fluidic connection 3 to the remotely located measuring location 80. The pumping device 7" further has, as the pump, the bidirectionally delivery pump 71 as in FIG. 1a. In addition, a flow sensor 90 is arranged in the internal gas guide element 3' in the flow path to the remotely located measuring location 80 in this FIG. 1c.

The pressure sensor 6 is shown in FIGS. 1b and 1c as a part of the pumping devices 7', 7", which part is configured to detect measured values of a pressure 77 at the gas guide element 3 and to transmit these measured values 77 to the control unit 70. The control unit 70 is able by means of the measured values of the pressure 77 to control the pump 74, 71 in terms of delivery pressure and/or flow rate. For example, a pump motor driving the pump 74, 71 can be controlled or regulated for this by the control unit 70 by means of characteristics [P=F(n), n=F(U)] at a speed of rotation n corresponding to the flow rate (U) or to the delivery pressure by means of the control signal 76, configured as current, voltage or a PWM signal with inclusion of the measured values of the pressure 77. The pump 71 (FIG. 1c) may also be controlled in terms of the direction of delivery by the control unit 70.

FIGS. 2a and 2b show a third variant 7''' of the pumping device according to the testing device 1 shown in FIG. 1a in a first operating state (FIG. 2a) and in a second operating state (FIG. 2b). FIGS. 2a and 2b are explained in a joint description. Identical components in FIGS. 1a, 2a and 2b are designated by the same reference numbers in FIGS. 1a, 2a, 2b. The first operating state corresponds to the first operating state 65 according to FIG. 1a and it makes it possible to deliver test gas 91 from the test gas source 9 to the remotely located measuring location 80. The second operating state corresponds to the second operating state 66 according to FIG. 1a and it makes possible a return delivery from the remotely located measuring location 80 to the pumping device 7''' and to the gas sensor 5. The pumping device 7''' has a unidirectionally delivering pump 74, which is connected to an array of two so-called 3/2-way valves 51, 53 by means of internal gas guide elements 3'.

The 3/2-way valves 51, 53 can be put by the control unit 70 into two different states of flow. These states of flow of the 3/2-way valves 51, 53 can be set by the control unit 70 by means of control signals 76 and switching elements 70' belonging to the valves 51, 53, so that the direction of delivery of the pumping device 7''' is reversible, i.e., a gas quantity 93 of test gas 91 delivered from the test gas source 9 to the remotely located measuring location 80 in the first operating state (FIG. 2a), or the quantity of gas 93 with the test gas 91 is delivered from the remotely located measuring location 80 back to the pumping device 7' and to the gas sensor 5. To avoid a state in which test gas 91 can directly reach the gas sensor 5 from the test gas source 9 or is delivered by means of the pump 74, a 2/2-way valve 52 is arranged at the test gas source 9. The control unit 70 can activate a switching element 70' on the valve 52 by means of a control signal 76 in order to open the valve 52, so that test gas 91 can enter the internal gas guide element 3' for being fed to the valves 51, 53. The control unit 70 configures the two operating states 65 (FIG. 1a, FIG. 2a) and 66 (FIG. 1a, FIG. 2b) by means of controlling the switching elements 70' on the valves 51, 52, 53 by means of the control signals 76 as they arise from the differences in the valve positions shown in FIGS. 2a and 2b. Measured values 77 detected by the gas sensor 5 are analyzed by the control unit 70 for performing the testing of the operational capability of the gas guide element 3, as was described above in connection with FIG. 1a.

A fourth variant 79 of the pumping device according to the testing device 1 shown in FIG. 1a is shown in FIGS. 3a and 3b in a first operating state (FIG. 3a) and in a second operating state (FIG. 3b). FIGS. 3a and 3b are explained in a joint description of the figures. Identical components in FIGS. 1a, 3a, 3b are designated by the same reference numbers in FIGS. 1a, 3a, 3b. The first operating state corresponds to the first operating state 65 according to FIG. 1a and it makes possible the delivery of test gas 91 from the test gas source 9 by means of the gas guide element 3 to the remotely located measuring location 80. The second operating state corresponds to the second operating state 66 according to FIG. 1a and it makes possible a return delivery from the remotely located measuring location 80 back to the pumping device 79 and to the gas sensor 5. The pumping device 79 has an array of two unidirectionally delivering pumps 74, 75 in an antiparallel arrangement, which are connected by means of internal gas guide elements 3'. The two pumps 74, 75 can be activated separately by means of control signals 76, so that two directions of delivery can be obtained with the pumping device 79, depending on activation of the pumps 74. 75. The quantity of gas 93 of test gas 91 is delivered in the first operating state (FIG. 3a) from the test gas source 9 to the remotely located measuring location 80 by means of the gas guide element 3. In the second operating state (FIG. 3b), this quantity of gas 93 of test gas 91 is delivered from the remotely located measuring location 80 back to the pumping device 79 and to the gas sensor 5. To avoid a state in which the test gas 91 can directly reach the gas sensor 5 from the test gas source 9 or is delivered by means of the pump 74, a 2/2-way valve 52 is arranged at the test gas source. The control unit 70 can activate a switching element 70' on the valve 52 by means of a control signal 76 in order to open the valve 52, so that test gas 91 can enter from the test gas source 9 the internal gas guide element 3' for being fed to the two pumps 74, 75. To set the first operating state 65 (FIG. 1a, FIG. 3a), the control unit 70 activates the second pump 75 by means of the control signals 76 and opens the valve 52. The second pump 75 delivers the test gas 91 into the gas guide element 3 to the remotely located measuring location 80. The first pump 74 is deactivated in the first operating state 65 (FIG. 1a, FIG. 3a) and it does not deliver any quantities of gas. To set the second operating state 66 (FIG. 1a, FIG. 3b), the control unit 70 activates the first pump 74 and closes the valve 52 by means of the control signals 76. The first pump 75 delivers the test gas 91 from the remotely located measuring location 80 back to the gas sensor 5. The second pump 75 is deactivated in the second operating state 66 (FIG. 1a, FIG. 3b) and it does not deliver any quantities of gas. Measured values 77 detected by the gas sensor are analyzed by the control unit 70 for performing the testing of the operational capability of the gas guide element 3, as was described in connection with FIG. 1a above.

FIGS. 2a and 2b, 3a and 3b show a pressure sensor 6 as a respective part of the pumping device 79, which is configured to detect measured values of a pressure 77 at the gas guide element 3 and to transmit them to the control unit 70. By means of the measured values of the pressure 77, the control unit 70 is able to activate the pump 74 (FIGS. 2a, 2b) or the pumps 74, 75 (FIGS. 3a, 3b) and to control them in terms of the delivery pressure and/or the flow rate. The pump may be controlled in different ways, as is explained in the description of FIGS. 1b and 1c.

FIG. 4 shows a variant 79' of the testing device according to FIG. 3b with a gas outlet 13. The variant of the pumping device 79' is based on the configurations shown and described in connection with FIGS. 3a and 3b with two pumps 74, 75 arranged in an antiparallel arrangement, test gas source 9, control unit 70 and control signals 76, 2/2-way valve 52, gas sensor 5, pressure sensor 6, associated measured values 77, switching elements 70' and gas guide elements 3, 3' with fluidic connection to the remotely located measuring location 80. Identical components in FIGS. 1a, 3a, 3b, 4 are designated by the same reference numbers in FIGS. 1a, 3a, 3b, 4. The gas outlet 13 and the gas sensor 5 are connected fluidically to the first pump 74 by means of a 3/2-way valve 51. The 3/2-way valve 51 can be set for this by the control unit 70 into two different states of flow by means of a control signal 76. This makes it possible in the state of flow of the valve as shown in FIG. 4 either to feed the quantity of gas 93, which is delivered by means of the activated first pump 74 from the remotely located measuring location 80, to the gas sensor 5, or to send it through the gas outlet 13 into a surrounding area 130 by means of a gas discharge line. Another pressure sensor 6' is arranged in this FIG. 4 at the inlet of the valve 51 and at the outlet of the pump 74, and the measured value 77 of this pressure sensor 6' is provided to the control unit 70, so that the control unit 70 is able to take into consideration a current delivery pressure of the pump 74 by means of the measured values 77 in the manner of switchover of the quantity of gas 93 delivered from the remotely located measuring location 80 into the gas outlet 13 or to the gas sensor 5. The possibility of switchover of the quantity of gas 93 delivered from the remotely located measuring location 80 into the gas outlet 13 offers the advantage that the gas sensor 5 can be uncoupled from scavenging gas, measured gas or test gas by means of the control signal 76 by the control unit 70 at any time during the testing of the operational capability of the gas guide element 3, so that, for example, a testing, resetting, adjustment (offset, characteristic) or calibration of the gas sensor 5 can be performed or prompted by the control unit 70 even during the ongoing testing of the operational capability of the gas guide element 3. Furthermore, the arrangement of the gas outlet 13 with the associated 3/2-way valve 51 offers the advantage that scavenging of the gas-measuring system 11 (FIG. 1a), of the pumping device 79' as well as of the gas guide element 3 can be carried out, as is described in connection with FIG. 1a, with the scavenging gas 91' (FIG. 1a) by means of a scavenging gas 91' (FIG. 1a) from a scavenging gas source 9' (FIG. 1a) without the scavenging gas 91' (FIG. 1a) having to be fed to the gas sensor. This leads to the advantage that there are no waiting times or recovery times of the gas sensor 5 for detecting the measured gas by the gas sensor 5 in the course of the further operation after the scavenging of the gas guide element 3.

FIG. 5 shows a variant 79'' of the device according to FIG. 3b with another gas sensor 5'. Identical components in FIGS. 1a, 3a, 3b, 5 are designated by the same reference numbers in FIGS. 1a, 3a, 3b, 5. The variant of the pumping device 79'' is based on the configurations shown and described in connection with FIGS. 3a and 3b with the two pumps 74, 75 arranged in an antiparallel arrangement, test gas source 9, control unit 70 and control signals 76, 2/2-way valve 52, gas sensor 5, pressure sensor 6, measured values 77, switching elements 70' and gas guide elements 3, 3' with fluidic connection to the remotely located measuring location 80 of the gas-measuring system 11 (FIG. 1a).

The additional gas sensor 5' and the gas sensor 5 are connected in this FIG. 5 to the first pump 74 by means of a 3/2-way valve 51. The 3/2-way valve 51 can be put by the control unit 70 with a control signal 76 into two different states of flow. This makes it possible in this shown state of flow of the valve 51 according to FIG. 5 that the quantity of gas 93, which is delivered by means of the activated first pump 74 from the remotely located measuring location 80, is fed either to the gas sensor 5 or to the additional gas sensor 5'.

The possibility of switching the quantity of gas 93 delivered from the remotely located measuring location 80 to the gas sensor 5 or to the additional gas sensor 5' offers the advantage that the test gas 91 is not admitted to the gas sensor 5, which is configured to detect the measured gas, for testing the operational capability of the gas guide element 3. This is made possible by the fact that the additional gas sensor 5' is used to test the operational capability of the gas guide element 3. Thus, an additional advantage of the additional gas sensor 5' is that the measured gas itself does not need to be used as the test gas 91 to test the operational capability of the gas guide element 3, but another gas can be used as a test gas 91 with any test gas 91 concentration adapted to the performance of the testing of the gas guide element 3 in the gas-measuring system 11 (FIG. 1a).

While specific embodiments of the invention have been shown and described in detail to illustrate the application of the principles of the invention, it will be understood that the invention may be embodied otherwise without departing from such principles.

APPENDIX

List of Reference Numbers

1 Device
3 Gas guide element (hose line)
3' Internal gas guide elements in the pumping device 7
5, 5' Gas sensor
6, 6' Pressure sensor
7, 7', 7'', 7''', 79, 79', 79'' Pumping device
9 Test gas source, test gas tank, gas generator
9' Scavenging gas source
11 Gas-measuring system
13 Gas outlet
33 Technical properties of the gas guide element
34 Length of the gas guide element to the measuring location
51 First 3/2-way valve
52 Second 3/2-way valve
53 2/2-way valve
61, 62, 63, 64 Steps of the sequence of steps
65 First operating state
66 Second operating state
67 Additional operating state
69 Memory
70 Control unit
70' Switching elements
71 Bidirectionally delivering pump
70' Switching elements
72 Current measured value at the start of the second operating state
72' Current measured value at the end of the second operating state
73 Technical properties of the pumping device
74 First pump (unidirectional)
75 Second pump (unidirectional)
76 Control signals, activating signals, switching signals
77 Measured values, set of measured values
78 First comparison data value
78' Second comparison data value
80 Remote measuring location
81 First predefined time period
82 Second predefined time period
85 Comparison criterion
86 Indicator of operational capability
88 Output signal
89, 89' Leak A
90 Flow sensor
91 Quantity of test gas
91' Quantity of scavenging gas 91" Test gas stored in the liquid state
93 Quantity of gas
100 Output and alarm generation unit
101 Analysis system in data network
130 Surrounding area

What is claimed is:

1. An operational capability determination device for determining an operational capability of a gas guide element of a gas-measuring system, which gas guide element is configured to route or guide a fluid, which gas-measuring system comprises the gas guide element, at least one gas sensor and a pumping device, the operational capability determination device comprising:
   a test gas source; and
   a control unit with an associated memory and operative connections to the pumping device and the at least one gas sensor, wherein:
   the gas guide element extending between the pumping device and at least one gas sensor and extending to a measuring location, located at a distance from the gas sensor;
   the gas guide element, the at least one gas sensor and the pumping device are fluidically connected to one another and are configured for interaction such that a quantity of gas can be fed to the at least one gas sensor from the measuring location, located at a distance from the gas sensor, and a quantity of gas can be fed from the pumping device to the measuring location;
   the test gas source is arranged at the pumping device and the gas guide element;
   the at least one gas sensor and the pumping device are connected fluidically such that a quantity of test gas can be fed as a quantity of test gas from the test gas source to the measuring location;
   the control unit is configured to receive measured values, which are detected and provided by the at least one gas sensor and indicate gas concentrations;
   the control unit is configured with the associated memory to store the measured values detected and provided by the at least one gas sensor;
   the control unit is configured to determine the operational capability of the gas guide element, to coordinate the pumping device in interaction with the at least one gas sensor by means of a sequence of steps beginning from a measuring operation, the sequence of steps comprising:
   the control unit putting the pumping device into a first operating state for a first predefined time period so that a quantity of test gas is delivered from the test gas source to the gas guide element and fed toward the measuring location by means of the gas guide element and selecting a duration of the first predefined time period based on technical properties of the gas guide element and based on technical properties of the pumping device such that the gas guide element is filled with the test gas over a length of the gas guide element from the measuring location to the pumping device;
   the control unit putting the pumping device into a second operating state for a predefined time period so that a quantity of gas is delivered from the gas guide element to the at least one gas sensor and fed away from the measuring location by means of the gas guide element and selecting a duration of the second predefined time period based on the first predefined time period and based on technical properties of the gas guide element and based on technical properties of the pumping device;
   the control unit receiving a plurality of measured values provided by the at least one gas sensor during the second predefined time period, and the control unit storing in the memory a beginning current measured value of the provided measured values as a first comparison data value at the beginning of the second predefined time period and the control unit storing in the memory an end current measured value of the provided measured values as a second comparison data value at the end of the second predefined time period;
   the control unit performing a comparison between the first comparison data value and the second comparison data value and determining an indicator of the operational capability of the gas guide element based on the comparison between the first comparison data value and the second comparison data value and a predefined comparison criterion; and
   the control unit determining an output signal, which indicates the indicator of the operational capability of the gas guide element and the control unit providing the output signal as an output.

2. A device in accordance with claim 1, further comprising a scavenging gas source arranged at the pumping device, wherein:
   the scavenging gas source, the gas guide element, the at least one gas sensor and the pumping device are connected fluidically such that a quantity of scavenging gas can be fed as a quantity of gas to the at least one gas sensor from the scavenging gas source; and
   before the pumping device is put by the control unit, for the first predefined time period, into the first operating state, the control unit is put into an expanded operating state for the first predefined time period, so that a quantity of scavenging gas is delivered from the scavenging gas source to the gas guide element toward the measuring location by means of the gas guide element, so that the gas guide element is completely filled with the scavenging gas over the length from the measuring location to the pumping device.

3. A device in accordance with claim 2, wherein:
   a 2/2-way valve is arranged in or at the pumping device, the test gas source or the scavenging gas source; and
   the 2/2-way valve is has a state that is controlled by the control unit by means of a control signal such that test gas or scavenging gas is delivered as a quantity of gas to the gas guide element in a direction toward the measuring location and no test gas or scavenging gas is directly delivered or can reach the at least one gas sensor from the test gas source, the scavenging gas source or the pumping device.

4. A device in accordance with claim 2, wherein
   the test gas source and/or the scavenging gas source are provided as a configuration of a container with an array of valves, switching devices or piezo dispensing elements; and
   the valves, switching devices or piezo dispensing elements can be activated by the control unit by means of control signals such that the test gas and/or the scavenging gas is provided, sent or fed to the pumping device.

5. A device in accordance with claim 1, wherein the pumping device comprises a bidirectionally delivering pump with a direction of delivery that can be reversed by the control unit by means of a control signal, and the bidirectionally delivering pump is configured so that either a quantity of gas is delivered from the gas guide element to the pumping device and fed away from the measuring location and to the at least one gas sensor or a quantity of test gas is delivered from the test gas source to the gas guide element and fed toward the measuring location.

6. A device in accordance with claim 1, wherein:
   the pumping device comprises an array of two 3/2-way valves; and
   the control unit sets respective states of flow of the 3/2-way valves by means of control signals such that either a quantity of measured gas is delivered from the gas guide element and fed away from the measuring location to the pumping device and to the at least one gas sensor or a quantity of test gas is delivered from the test gas source to the gas guide element and fed toward the measuring location.

7. A device in accordance with claim 1, wherein:
   the pumping device is configured as an arrangement of two pumps arranged in an antiparallel arrangement; and
   the control unit activates by means of a control signal either one pump or the other pump, so that either a quantity of measured gas is delivered from the gas guide element and fed from the measuring location to the pumping device and to the at least one gas sensor or a quantity of test gas is delivered from the test gas source to the gas guide element and fed toward the measuring location.

8. A device in accordance with claim 1, wherein:
   the at least at least one sensor is a part of a sensor system that further comprises an additional gas sensor fluidically connected to the pumping device such that a quantity of gas can be fed to the additional gas sensor from the gas guide element and in a direction from the measuring location; and
   the additional gas sensor responds to changes in gas concentration of the test gas with a change in a gas concentration measured value.

9. A device in accordance with claim 8, wherein:
   a 3/2-way valve is arranged between the pumping device and the at least one gas sensor and the additional gas sensor; and
   a state of flow of the 3/2-way valve is set by the control unit by means of a control signal such that delivery of the quantity of gas from the gas guide element in a direction from the measuring location, to the at least one gas sensor or delivery of the quantity of gas from the gas guide element in a direction from the measuring location, to the additional gas sensor is possible.

10. A device in accordance with claim 1, further comprising a gas outlet, wherein
    a 3/2-way valve is arranged in the pumping device; and
    a state of flow of the 3/2-way valve is set by the control unit by means of a control signal such that delivery of the quantity of gas from the gas guide element in a direction from the measuring location, to the at least one gas sensor or delivery of the quantity of gas from the gas guide element in the direction from the measuring location, into the gas outlet is possible.

11. A device in accordance with claim 1, wherein the test gas source is configured as a gas generator, which is activated by the control unit by means of a control signal and the gas generator is configured to generate the test gas electrolytically, chemically or electrochemically.

12. A device in accordance with claim 1, wherein:
    the test gas source is configured as a pressure tank with a shut-off valve;
    the test gas is stored in the pressure tank under admission pressure in a liquid state and is provided for the pumping device for delivery to the gas guide element in a direction toward the measuring location; and
    the shut-off valve is controlled by the control unit by means of a control signal such that flow from the pressure tank to the measuring location is brought about and made possible.

13. A device in accordance with claim 1, further comprising a pressure sensor configured to detect pressure of a quantity of gas present in the gas guide element and to provide the detected pressure to the control unit as a measured value of the pressure, wherein:
    the pressure sensor is arranged in or close to the pumping device at the gas guide element; and
    the control unit is configured to control the pumping by the pumping device in terms of a delivery rate and/or a flow rate and/or a delivery pressure by means of a control signal based on the measured value.

14. A device in accordance with claim 1, further comprising a flow sensor configured to detect flow rates of a quantity of gas flowing in the gas guide element and to provide detected flow rates as measured values to the control unit, wherein:
    the flow sensor is arranged in or close to the pumping device in the gas guide element; and
    the control unit is configured to control the pump or the pumps in the pumping device in terms of a delivery rate and/or a flow rate based on the measured value by means of a control signal.

* * * * *